US010391216B2

(12) United States Patent
Wildhirt et al.

(10) Patent No.: US 10,391,216 B2
(45) Date of Patent: Aug. 27, 2019

(54) SUPPORTING A HEART

(71) Applicant: AdjuCor GmbH, Garching bei München (DE)

(72) Inventors: Stephen Manuel Wildhirt, Munich (DE); Andreas Maier, Munich (DE)

(73) Assignee: AdjuCor GmbH, Munich (DE)

( * ) Notice: Subject to any disclaimer, the term of this patent is extended or adjusted under 35 U.S.C. 154(b) by 84 days.

(21) Appl. No.: 13/839,845

(22) Filed: Mar. 15, 2013

(65) Prior Publication Data

US 2014/0194672 A1   Jul. 10, 2014

(30) Foreign Application Priority Data

Jan. 8, 2013   (DE) .................. 10 2013 200 148

(51) Int. Cl.
| | | |
|---|---|---|
| *A61N 1/362* | (2006.01) | |
| *A61M 1/10* | (2006.01) | |
| *A61M 1/12* | (2006.01) | |
| *A61M 39/10* | (2006.01) | |
| *A61M 39/02* | (2006.01) | |

(52) U.S. Cl.
CPC .......... *A61M 1/106* (2013.01); *A61M 1/1008* (2014.02); *A61M 1/1086* (2013.01); *A61M 1/1068* (2013.01); *A61M 1/12* (2013.01); *A61M 1/127* (2013.01); *A61M 39/0247* (2013.01); *A61M 2039/027* (2013.01); *A61M 2039/0267* (2013.01); *A61M 2039/0273* (2013.01); *A61M 2039/0276* (2013.01); *A61M 2039/1022* (2013.01)

(58) Field of Classification Search
CPC .... A61M 1/106; A61M 1/122; A61M 1/1037; A61M 1/1068; A61M 1/107; A61M 1/1086; A61F 2/2481; A61F 2250/0003
See application file for complete search history.

(56) References Cited

U.S. PATENT DOCUMENTS

| 2,815,715 A | 12/1957 | Tremblay |
|---|---|---|
| 3,053,249 A | 9/1962 | Smith |

(Continued)

FOREIGN PATENT DOCUMENTS

| DE | 69427906 T2 | 4/2002 |
|---|---|---|
| DE | 102009043795 A1 | 3/2011 |

(Continued)

OTHER PUBLICATIONS

Kaden, Malte, Examination Report for European Patent Application No. 10765952.6, dated Jan. 14, 2014, 5 pages.

(Continued)

*Primary Examiner* — Lindsey G Wehrheim
(74) *Attorney, Agent, or Firm* — Gardella Grace P.A.

(57) ABSTRACT

A heart support system featuring a constraint sized to fit about at least a portion of an adult human heart in a living body, an expandable chamber disposed within the constraint so as to apply pressure against the heart when expanded and a connector system including a pneumatic connection port in hydraulic communication with the expandable chamber. The heart support system can include a supply unit with: a source of pressurized fluid and a pneumatic supply line extending from the pressurized fluid source. The pneumatic supply line is connectable to the pneumatic connection port.

21 Claims, 18 Drawing Sheets

(56) References Cited

U.S. PATENT DOCUMENTS

| | | | |
|---|---|---|---|
| 3,663,965 A * | 5/1972 | Lee, Jr. | A61M 39/0247 604/175 |
| 4,381,567 A * | 5/1983 | Robinson | A61M 1/1037 417/383 |
| 4,503,857 A * | 3/1985 | Boute | A61N 1/365 607/16 |
| 4,536,893 A * | 8/1985 | Parravicini | A61M 1/1062 601/153 |
| 5,273,518 A | 12/1993 | Lee et al. | |
| 5,350,419 A * | 9/1994 | Bendel et al. | 607/132 |
| 5,490,820 A | 2/1996 | Schock | |
| 5,533,958 A * | 7/1996 | Wilk | A61B 17/00234 600/18 |
| 5,613,935 A * | 3/1997 | Jarvik | A61M 1/101 600/16 |
| 5,728,134 A | 3/1998 | Barak | |
| 5,749,839 A | 5/1998 | Kovacs | |
| 5,797,960 A | 8/1998 | Stevens et al. | |
| 6,059,750 A * | 5/2000 | Fogarty | A61M 1/1068 601/153 |
| 6,126,590 A | 10/2000 | Alferness | |
| 6,258,021 B1 | 7/2001 | Wilk | |
| 6,334,871 B1 | 1/2002 | Dor et al. | |
| 6,432,039 B1 * | 8/2002 | Wardle | A61F 2/2481 600/16 |
| 6,540,659 B1 | 4/2003 | Milbocker | |
| 6,540,666 B1 | 4/2003 | Chekanov | |
| 6,572,534 B1 | 6/2003 | Milbocker et al. | |
| 6,602,182 B1 | 8/2003 | Milbocker | |
| 6,612,979 B2 | 9/2003 | Lau et al. | |
| 6,626,821 B1 * | 9/2003 | Kung | A61M 1/122 600/16 |
| 6,669,674 B1 | 12/2003 | Macoviak et al. | |
| 6,723,041 B2 | 4/2004 | Lau et al. | |
| 6,730,016 B1 | 5/2004 | Cox et al. | |
| 6,840,246 B2 | 1/2005 | Downing | |
| 7,175,652 B2 | 2/2007 | Cook et al. | |
| 7,637,880 B2 | 12/2009 | Ferrari | |
| 7,841,976 B2 | 11/2010 | McBride et al. | |
| 7,850,729 B2 | 12/2010 | Melvin | |
| 8,002,820 B2 | 8/2011 | Kaufmann | |
| 8,944,987 B2 | 2/2015 | Meister et al. | |
| 9,220,824 B2 | 12/2015 | Wildhirt et al. | |
| 2002/0019580 A1 | 2/2002 | Lau et al. | |
| 2002/0045799 A1 | 4/2002 | Lau et al. | |
| 2002/0065449 A1 | 5/2002 | Wardle | |
| 2003/0229260 A1 | 12/2003 | Girard | |
| 2003/0229266 A1 | 12/2003 | Cox et al. | |
| 2004/0002626 A1 | 1/2004 | Feld et al. | |
| 2004/0044399 A1 | 3/2004 | Ventura | |
| 2004/0064014 A1 | 4/2004 | Melvin et al. | |
| 2004/0102804 A1 | 5/2004 | Chin | |
| 2004/0117032 A1 | 6/2004 | Roth | |
| 2004/0225177 A1 * | 11/2004 | Coleman et al. | 600/17 |
| 2004/0267329 A1 | 12/2004 | Raman et al. | |
| 2005/0107661 A1 | 5/2005 | Lau et al. | |
| 2005/0148814 A1 | 7/2005 | Fischi et al. | |
| 2005/0192483 A1 | 9/2005 | Bonadio et al. | |
| 2005/0197527 A1 | 9/2005 | Bolling | |
| 2005/0283042 A1 | 12/2005 | Meyer et al. | |
| 2006/0074484 A1 | 4/2006 | Huber | |
| 2006/0167334 A1 * | 7/2006 | Anstadt et al. | 600/17 |
| 2006/0189840 A1 * | 8/2006 | Walsh et al. | 600/16 |
| 2006/0217774 A1 | 9/2006 | Mower et al. | |
| 2007/0185369 A1 | 8/2007 | Mirhoseini et al. | |
| 2007/0197859 A1 | 8/2007 | Schaer et al. | |
| 2007/0225545 A1 | 9/2007 | Ferrari | |
| 2007/0270654 A1 | 11/2007 | Pignato et al. | |
| 2008/0021266 A1 | 1/2008 | Laham | |
| 2008/0064917 A1 | 3/2008 | Bar et al. | |
| 2008/0081944 A1 | 4/2008 | Lau et al. | |
| 2008/0214888 A1 | 9/2008 | Ben | |
| 2008/0255647 A1 * | 10/2008 | Jensen et al. | 607/119 |
| 2008/0275294 A1 | 11/2008 | Gertner | |
| 2008/0319255 A1 | 12/2008 | Cohn | |
| 2009/0036730 A1 | 2/2009 | Criscione et al. | |
| 2009/0138070 A1 | 5/2009 | Holzer et al. | |
| 2009/0326332 A1 | 12/2009 | Carter | |
| 2010/0030017 A1 | 2/2010 | Baker | |
| 2010/0100043 A1 | 4/2010 | Racenet | |
| 2010/0152523 A1 | 6/2010 | MacDonald et al. | |
| 2010/0160725 A1 | 6/2010 | Kiser et al. | |
| 2010/0256441 A1 | 10/2010 | Lu | |
| 2010/0261974 A1 | 10/2010 | Shelton, IV et al. | |
| 2010/0262080 A1 | 10/2010 | Shelton, IV et al. | |
| 2011/0004046 A1 | 1/2011 | Campbell et al. | |
| 2011/0021864 A1 | 1/2011 | Criscione et al. | |
| 2011/0270331 A1 * | 11/2011 | Peters | A61M 1/1068 607/3 |
| 2011/0275883 A1 | 11/2011 | Peters | |
| 2011/0298304 A1 * | 12/2011 | Cotter | A61M 1/127 307/147 |
| 2012/0130181 A1 | 5/2012 | Davis | |
| 2012/0130485 A1 | 5/2012 | Lillehei | |
| 2012/0142996 A1 | 6/2012 | Criscione | |
| 2012/0157781 A1 | 6/2012 | Kleyman | |
| 2012/0283506 A1 | 11/2012 | Meister | |
| 2012/0283507 A1 | 11/2012 | Lillehei | |
| 2013/0012938 A1 | 1/2013 | Asirvatham et al. | |
| 2013/0053623 A1 | 2/2013 | Evans et al. | |
| 2014/0107406 A1 | 4/2014 | Hjelle et al. | |
| 2014/0194669 A1 | 7/2014 | Wildhirt et al. | |
| 2014/0194670 A1 | 7/2014 | Wildhirt et al. | |
| 2014/0194672 A1 | 7/2014 | Wildhirt et al. | |
| 2014/0194678 A1 | 7/2014 | Wildhirt | |
| 2014/0194717 A1 | 7/2014 | Wildhirt et al. | |
| 2017/0007403 A1 | 1/2017 | Wildhirt et al. | |
| 2017/0007404 A1 | 1/2017 | Wildhirt et al. | |

FOREIGN PATENT DOCUMENTS

| | | |
|---|---|---|
| EP | 0700279 | 3/1996 |
| EP | 1880695 | 1/2008 |
| EP | 1748809 B1 | 11/2008 |
| WO | WO1998030271 A1 | 7/1998 |
| WO | 9855165 | 12/1998 |
| WO | WO2000025842 A1 | 5/2000 |
| WO | 0036995 | 6/2000 |
| WO | 2005091860 | 10/2005 |
| WO | 2005110514 | 11/2005 |
| WO | 2008151088 | 12/2008 |
| WO | WO2010042016 A1 | 4/2010 |
| WO | 2011075328 | 6/2011 |

OTHER PUBLICATIONS

Van Veen, Jennifer, Examination Report for European Patent Application No. 14150491 dated Apr. 11, 2014, 5 pages.

European Search Report for European Patent Application No. 14150491, dated Mar. 28, 2014, 5 pages.

Porter, Jr., Gary A., USPTO Non-Final Office Action in U.S. Appl. No. 13/838,517, dated May 23, 2014, 13 pages.

Baria, Dinah N., USPTO Non-Final Office Action in U.S. Appl. No. 13/838,528, dated Mar. 27, 2015, 14 pages.

Non-Final Office Action issued in U.S. Appl. No. 13/838,743 dated Jul. 9, 2015, 11 pages.

Non-Final Office Action issued in U.S. Appl. No. 13/838,517 dated May 23, 2014, 13 pages.

Non-Final Office Action issued in U.S. Appl. No. 13/839,455 dated Nov. 16, 2017, 55 pages.

Final Office Action issued in U.S. Appl. No. 13/839,455 dated Apr. 20, 2017, 42 pages.

Final Office Action issued in U.S. Appl. No. 13/838,528 dated Nov. 14, 2017, 34 pages.

Notice of Allowance issued in U.S. Appl. No. 13/838,831 dated Jul. 23, 2015, 47 pages.

Final Office Action issued in U.S. Appl. No. 13/838,528 dated Aug. 12, 2015, 26 pages.

Corrected Notice of Allowance issued in U.S. Appl. No. 13/838,831 dated Aug. 28, 2015, 17 pages.

(56) References Cited

OTHER PUBLICATIONS

Non-Final Office Action issued in U.S. Appl. No. 13/839,455 dated Sep. 8, 2015, 59 pages.
Non-Final Office Action issued in U.S. Appl. No. 13/838,528 dated Mar. 10, 2016, 26 pages.
Final Office Action issued in U.S. Appl. No. 13/839,455 dated May 20, 2016, 37 pages.
Final Office Action issued in U.S. Appl. No. 13/838,528 dated Aug. 25, 2016, 24 pages.
Non-Final Office Action issued in U.S. Appl. No. 13/839,455 dated Oct. 11, 2016, 32 pages.
Non-Final Office Action issued in U.S. Appl. No. 13/838,528 dated Mar. 16, 2017, 48 pages.
International Search Report and Written Opinion issued in PCT/EP2010/005947, including English Translation, dated Dec. 16, 2010, 22 pages.
ParaMount Mini GPS, Balloon Expandable Biliary Stent System, Copyright 2010, www.ev3.net, 4 pages.
Extended European Search Report for European Patent Application No. 15184605.2 dated Jan. 18, 2016, 7 pages.
Extended European Search Report for European Patent Application No. 16178130.7 dated Nov. 29, 2016, 7 pages.
Non-Final Office Action issued in U.S. Appl. No. 13/393,420 dated Jun. 25, 2014.
Notice of Allowance issued in U.S. Appl. No. 13/393,420 dated Sep. 22, 2014.
Final Office Action issued in U.S. Appl. No. 13/838,517 dated Jan. 21, 2015.
Final Office Action issued in U.S. Appl. No. 13/839,455 dated Apr. 20, 2018.
Notice of Allowance issued in U.S. Appl. No. 13/839,455 dated Aug. 27, 2018.
Non-Final Office Action issued in U.S. Appl. No. 14/982,741 dated Mar. 23, 2017.
Notice of Allowance issued in U.S. Appl. No. 14/982,741 dated Jul. 13, 2018.
U.S. Appl. No. 13/393,420, filed Jul. 27, 2012, 2012/0283506, Nov. 8, 2012, Meister.
U.S. Appl. No. 13/838,517, filed Mar. 15, 2013, Wildhirt.
U.S. Appl. No. 13/839,455, filed Mar. 15, 2013, Wildhirt.
U.S. Appl. No. 13/838,743, filed Mar. 15, 2013, Wildhirt.
U.S. Appl. No. 13/838,528, filed Mar. 15, 2013, Wildhirt.
U.S. Appl. No. 13/838,831, filed Mar. 15, 2013, Wildhirt.

* cited by examiner

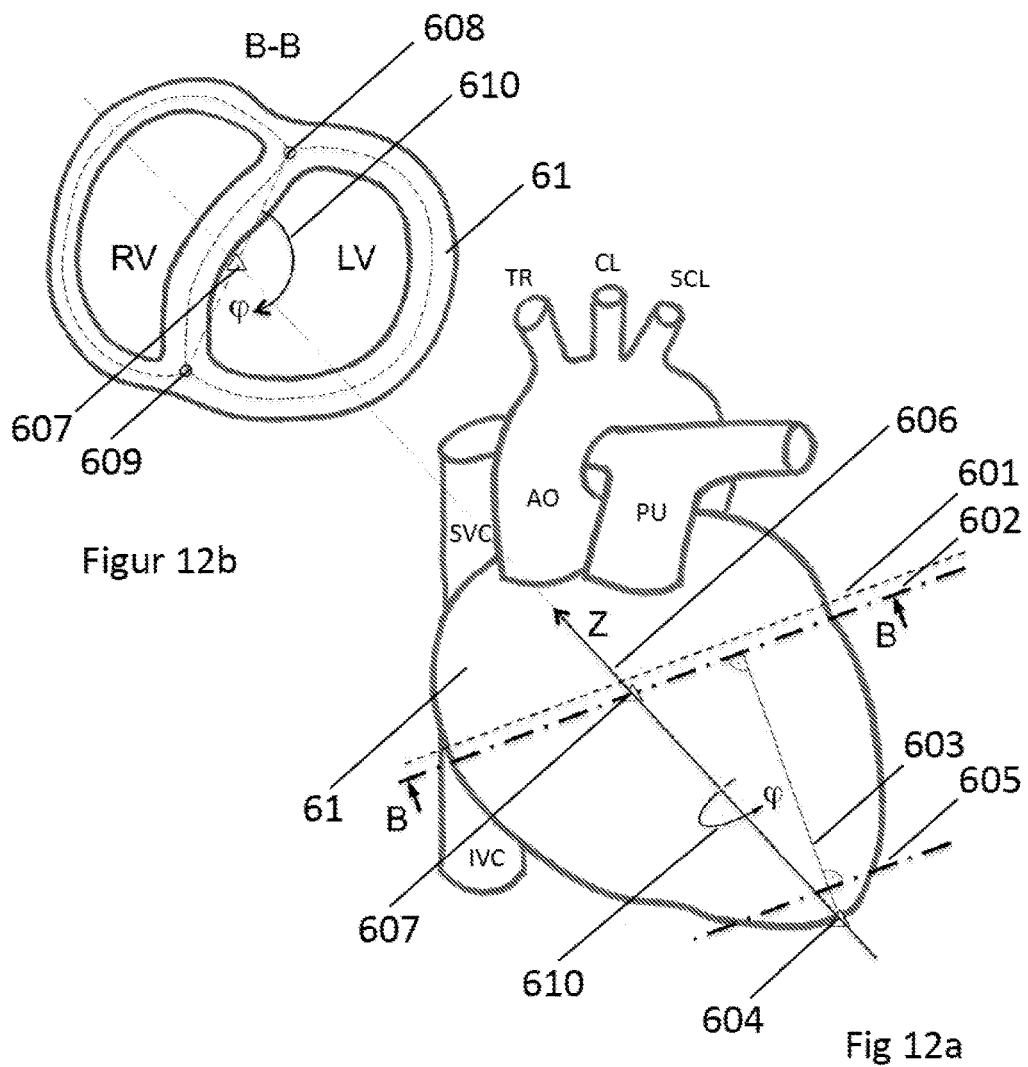

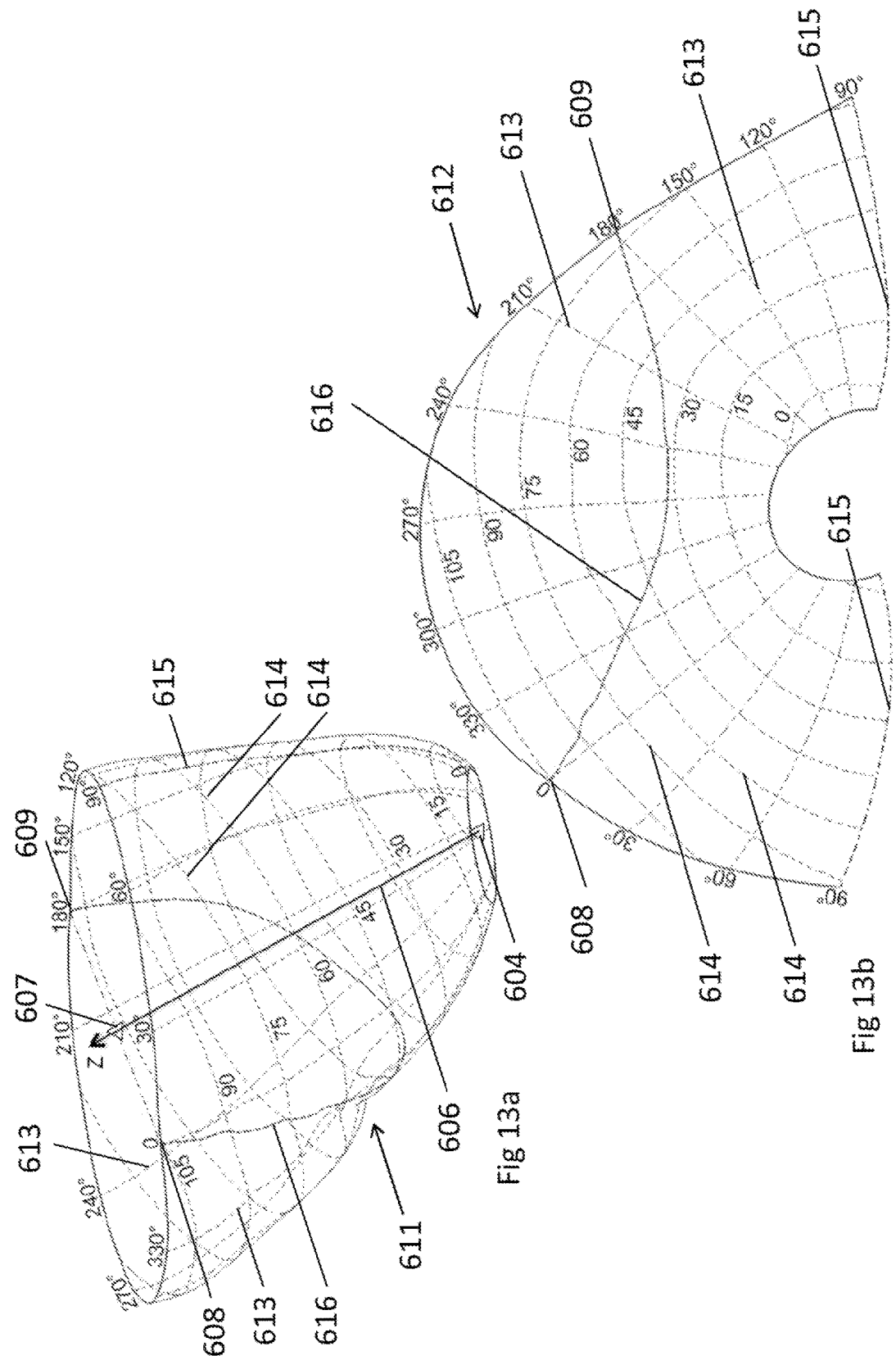

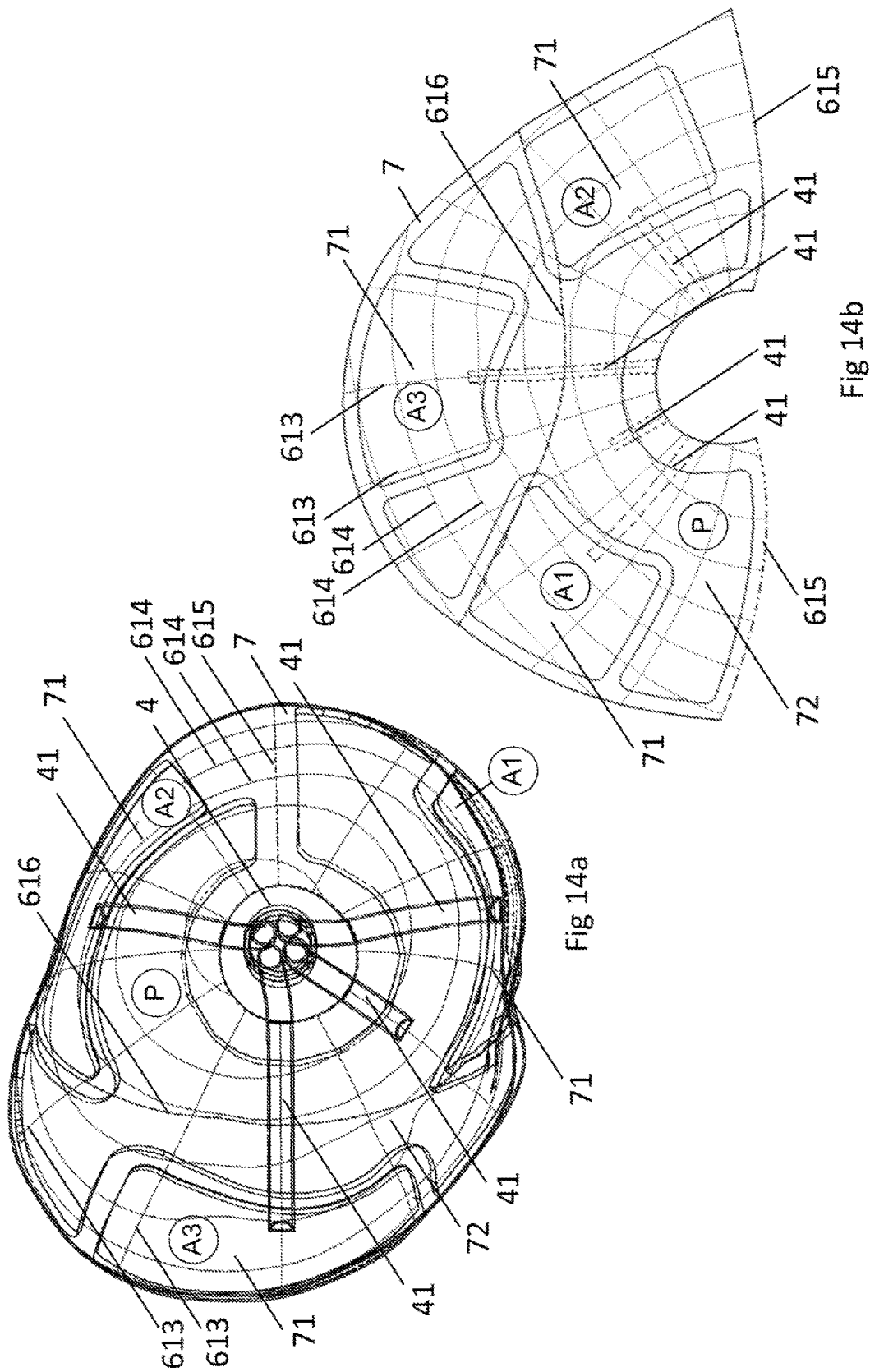

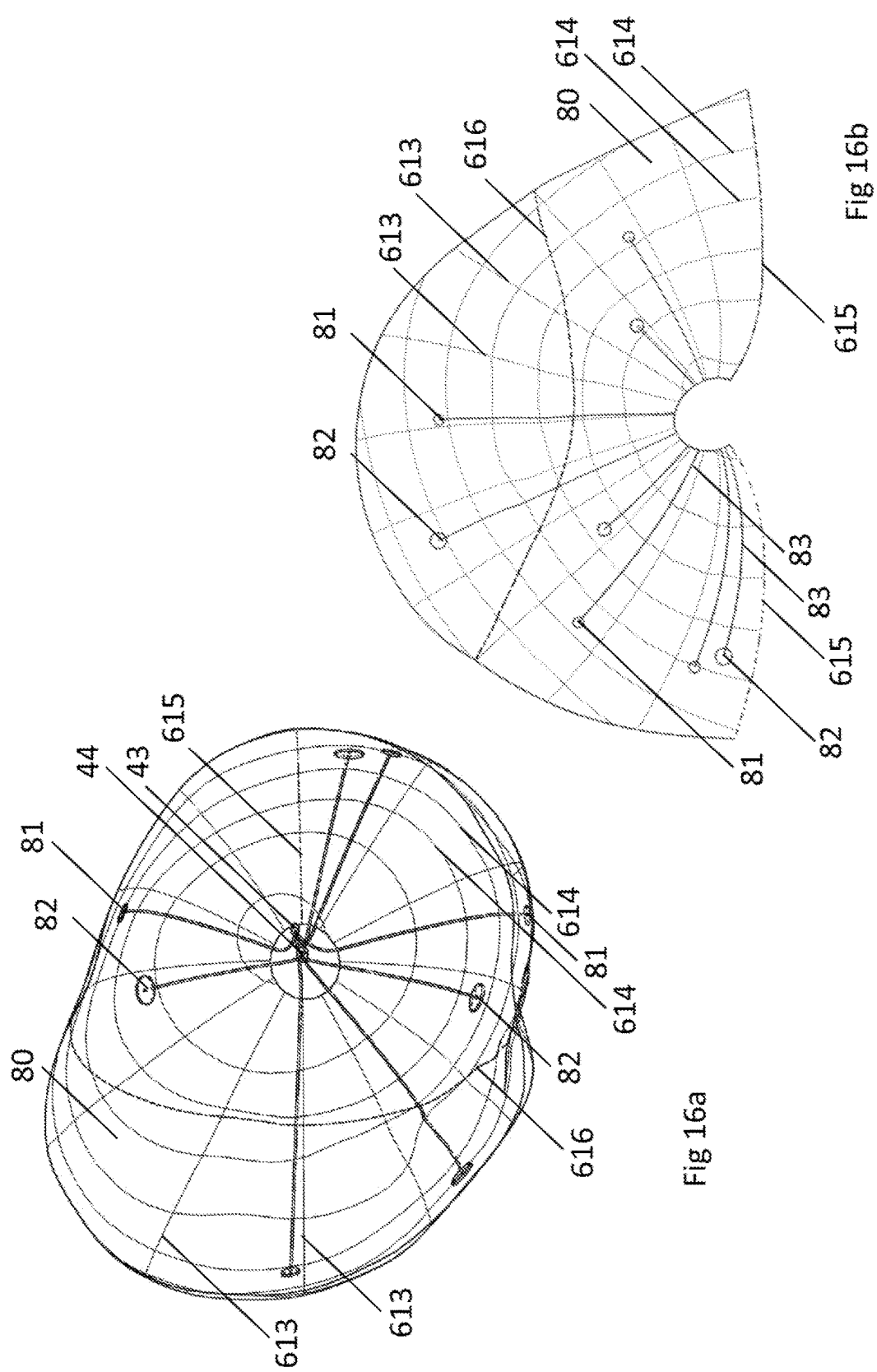

SUPPORTING A HEART

TECHNICAL FIELD

The invention pertains to a device to support cardiac function. In particular, the device according to the invention serves to support a pumping function of a heart.

BACKGROUND

Due to illness, the pumping function of a heart can be reduced, which is also called cardiac insufficiency. Cardiac insufficiency is from the medical as well as from the economical standpoint of great and increasing importance. In the second decade of this century, 23 million people worldwide will suffer from cardiac insufficiency; the annual rate of new cases will be about 2 million people. In the US alone, 5 million people are currently suffering from cardiac insufficiency. Here, the annual rate of new cases is approximately 550,000 people. Already in this decade, the number of incidences in people over 50 years of age will double to more than 10 million. The same applies to the European continent.

Causes for cardiac insufficiency can be impaired contractility or reduced filling of the cardiac chambers due to damage to the myocardium. Hypertension can lead to an increased pumping resistance, which can also negatively affect the pumping function of the heart. The pumping function of a heart can also be reduced by leaking valves (e.g., a leaking aortic valve or mitral valve). Impairments of the cardiac conduction system generate arrhythmias, which can also lead to a reduced pumping function of the heart. If the movement of the heart is restricted from the outside, e.g., due to an accumulation of fluid in the pericardium, this can result in a reduced pumping function as well. Cardiac insufficiency often leads to shortness of breath (especially in the case of left ventricular insufficiency), or to water retention in the lungs or in the abdomen (in particular in the case of right ventricular insufficiency).

Different types of cardiac insufficiencies are treatable with medication or surgery. In some cases of arrhythmias, normal cardiac rhythm can be restored with a pacemaker. A leaking valve can be replaced surgically with a cardiac valvular prosthesis. A reduced pumping function can be assisted by an implanted heart pump. A treatment approach addressing the various causes of heart insufficiency is to assist the pumping function of the heart by means of an implant, which exerts mechanical pressure onto the heart and therefore improves its pumping performance.

Some known mechanical ventricular assist devices have been disclosed in U.S. Pat. No. 5,749,839 B1 and U.S. Pat. No. 6,626,821 B1, and in WO application 00/25842. These documents disclose mechanical ventricular assist devices that require open-chest surgery. Many cardiac assist systems are complex and can only be implanted by means of an elaborate surgical procedure. All cardiac assist systems are integrated into the blood circulation of the patients. Improved centrifugal or magnetically supported impeller systems carry blood continuously. The contact of the blood with the surface of the implanted systems poses a great engineering and medical challenge. Common complications of cardiac assist systems are strokes, hemorrhage and septicemia. They often lead to long-term hospitalization and frequent re-admissions of patients already released from the hospital.

SUMMARY

Various aspects of the invention feature a heart support system having a constraint sized to fit about at least a portion of an adult human heart in a living body, an expandable chamber disposed within the constraint so as to apply pressure against the heart when expanded, and a connector system including a pneumatic connection port in hydraulic communication with the expandable chamber.

In several examples the system includes a sheath configured to transition from a non-expanded state into an expanded state, with the sheath being self-expanding and being configured to be inserted into a delivery system, and which in the expanded state can at least partially enclose a heart. One potential advantage of the device is that it may be implanted using minimally invasive procedures.

In some implementations, the sheath can be made of a wire mesh, which can have diamond-shaped cells. Preferably, the mesh is made of a shape memory alloy. The crossing points of the wires of the wire mesh can be permanently attached to each other, thus increasing the stability of the sheath. The crossing points may also be separable, which increases the flexibility of the sheath and thereby can make the sheath easier to compress. Or some of the crossing points may be permanently interconnected while other crossing points are not permanently interconnected. By selecting suitable crossing points to be permanently interconnected, and crossing points that are not permanently interconnected, the stability and flexibility of the sheath can be adjusted.

According to one aspect of the invention, the sheath can also consist of a lattice structure, with the lattice structure consisting of links, and multiple links defining one cell. The lattice structure exhibits a diamond-shaped lattice structure. The links and the intersections of the links exhibit enforcements in order to increase the stability of the sheath. The effect of the enforcements is similar to the effect of the interconnected crossing points in embodiments of the sheath in the form of a wire mesh. The links and the intersections can also be made of a thinner or weaker material in order to increase the flexibility of the sheath. The effect of a thinner or weaker material at intersections is similar to the effect of the non-interconnected intersections in embodiments of the sheath in the form of a wire mesh.

The sheath can also be made of a solid material, from which parts have been removed. For example, the sheath can be made of a tube or an individually shaped sheath sleeve, into which holes have been formed or cut. The holes can be formed such that the sheath exhibits increased stability in some areas, and increased flexibility in other areas.

Generally, areas of increased stability are desired in situations, in which the sheath acts as an abutment. Areas of greater flexibility can enable the natural motion of the heart. Increased flexibility is also advantageous for compressing the sheath into a delivery system.

The sheath generally exhibits openings being created by the wires of the wire mesh, the links of the lattice structure, or by the holes formed in the sheath sleeve. The openings can be rectangular, diamond-shaped or round. The cells or holes can have a pin opening of 1 mm to 50 mm. A pin opening is defined as the largest diameter of a pin, which can be pushed through a cell or a hole. Using the holes, the stability and flexibility of the sheath can be adjusted individually. The holes also allow the exchange of substances from the inside of the sheath with the outer environment of the sheath.

The sheath can be covered with a membrane; the membrane may, in particular, be made of polyurethane, silicon or polytetrafluorethylene (PTFE). The membrane can reduce the mechanical stress exerted by the sheath onto the pericardium or the myocardium. The membrane can also increase the biocompatibility of the sheath. A coating of the membrane with an active substance is also conceivable.

Another aspect of the present invention features a method of manufacturing a cardiac assist device. The method includes using a virtual or real image of a heart and forming a sheath based on the shape of the heart image.

The method can be used to manufacture a custom-made sheath. The shape of the sheath can match the form of the 3D-image of the surface of the heart, spatially stretched by a factor. In particular, the stretch factor can range from 1.01 to 1.2. A sheath applied to a true-to-scale real or virtual 3D image of the heart should exhibit a distance to the 3D image of 1 to 10 mm, in particular 2 to 8 mm, in particular 3 to 5 mm.

Additional features and advantages of the invention will be apparent from the description and drawings, and from the claims.

DESCRIPTION OF DRAWINGS

FIG. 12a shows a heart with anatomical points of reference.

FIG. 12b shows a cross-section of the heart from FIG. 12a.

FIG. 13a shows a 3D view of part of a heart with a system of coordinates.

FIG. 13b shows a 2D-rollout of the 3D view from FIG. 13a with a system of coordinates.

FIG. 14a shows a 3D view of a sleeve with augmentation and positioning units.

FIG. 14b shows a 2D rollout of a sleeve with augmentation and positioning units from FIG. 14a.

FIG. 16a shows a 3D view of a sleeve with sensors and/or electrodes.

FIG. 16b shows a 2D rollout of the sleeve with sensors and/or electrodes from FIG. 16a.

DETAILED DESCRIPTION

Figure 1:
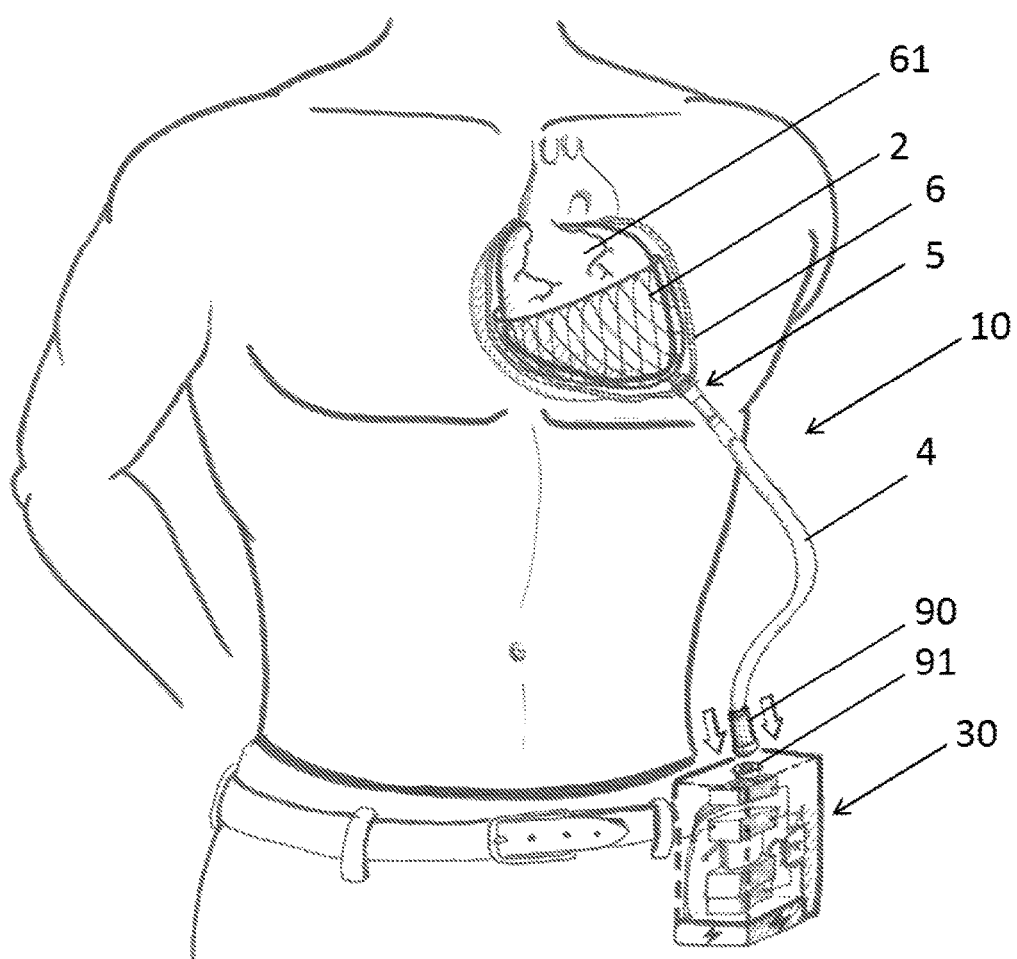
FIG. 1 shows a human torso with an implanted device and an extracorporeal supply unit.

FIG. 1 shows an embodiment (10) of a device in the implanted state. In this example, the device is implanted into a human body. The device, however, can also be implanted into an animal body, in particular into the body of a mammal like a dog, a cat, a rodent, a primate, an even-toed ungulates or an odd-toed ungulate. Depending on the species, the form and the mode of operation of the device is adjusted, in order to accommodate anatomical and/or physiological needs of the individual species.

FIG. 1 shows a human torso with the device. The device includes a sheath (2), which can at least partially enclose the heart (61). Multiple components inserted in the sheath (2) support the cardiac function (61). The device also includes a supply unit (30).

The sheath (2), which can at least partially enclose the heart (61), is configured to transition from a non-expanded state into an expanded state. Preferably, the sheath (2) is self-expanding and can be inserted into a delivery system in the non-expanded state. The sheath (2) can be a mesh, in particular a wire mesh, whereby the wire mesh can be at least partially made of a shape memory alloy.

The sheath (2) at least partially encloses the heart (61) in the implanted state and is located inside the pericardium (6). Embodiments in which the sheath (2) is placed outside of the pericardium (6) are possible as well. These embodiments are not described separately; rather, the description for embodiments for implantation inside and outside the pericardium (6) (with the exception of the not-required pericardial seal (5) in embodiments of the sheath (2) for implantation outside the pericardium (6)) is applicable. The architecture of the sheath (2) is explained in greater detail in a later section of the description.

Located inside the expandable sheath (2) is at least one expandable unit, which can be used to apply pressure to the heart (61). The expandable unit can be a mechanical unit, configured to transition between an expanded and a non-expanded state. Such a mechanical unit can include spring elements, which can be tensioned and released, or lever elements, which can be folded and unfolded. Preferably, the expandable units are chambers, which can be filled with a fluid. Suitable fluids for the filling of a chamber include liquids, gases, or solids (like nanoparticle mixtures, for example), or mixtures of fluids and/or gases and/or solids. The expandable unit can be secured inside the sheath (2). Preferably, the expandable unit is attached to a sleeve, which can be inserted into the sheath (2). The at least one expandable unit is described in greater detail with reference to FIG. 8.

The sheath (2) can furthermore include at least one sensor and/or one electrode, which can be used to detect at least one parameter of the heart (61). The sensor can be configured to determine the heart rate, the ventricular pressure, the contact force between the heart wall and the expandable unit, the systolic blood pressure, the diastolic blood pressure, the pressure applied to a surface of the heart, the fluid presence, the acidity, the electrical resistance, the osmolarity, the oxygen saturation or the flow through a vessel. The sensor can also be configured to measure the pressure applied by an expandable unit onto a surface, the pH-value, the electrical resistance, the osmolarity of a solution, the oxygen saturation of tissue or blood or the flow through a vessel. The sensor can be attached inside or on the sheath (2). Preferably, the sensor is secured on a sleeve configured to be inserted into the sheath (2). In addition to the at least one sensor or in place of the sensor, the sheath (2) can also include at least one electrode configured to measure a parameter, like e.g. the action potential at the myocardium during the excitation process, or to stimulate a tissue with currents. The sensor can also be an electrode. The sensor and the electrode are explained in greater detail in a later section of the description.

FIG. 1 shows a supply unit (30), which can be worn outside the body. The supply unit can also be partially or completely implanted into the body, which will be explained in the following sections in greater detail. If the supply unit (30) is worn outside the body, it may be attached to a chest belt, to a hip belt, or to an abdominal belt. The supply unit (30) is equipped with an energy storage device allowing the expandable unit to be powered. The energy storage device can be available in the form of a rechargeable battery providing electrical energy to expand the expandable unit. The rechargeable battery is exchangeable. The supply unit (30) can also include a pressure storage device supplying a compressed gas, to inflate an inflatable chamber. Suitable gases are, among others, compressed air, $CO_2$, or inert gases. The housing of the supply unit (30) itself can serve as a pressure storage housing. The supply unit (30) can furthermore contain pumps, valves, sensors and displays. The supply unit (30) can furthermore include a microprocessor configured to receive and process data from the at least one sensor. If the supply unit (30) is worn outside the body, the required energy can be transferred by direct connection via a cable (4) or connectionless via electromagnetic induction, for example. The data from the at least one sensor can also be transmitted directly via a cable (4) or connectionless via wireless technology like bluetooth, for example.

The device can furthermore include a cable (4) connecting the expandable unit and/or the sensor or the electrode to the supply unit (30). If the supply unit (30) is connected directly to the expandable unit and/or to the sensor, or the electrode, a cable (4) is not required. If the expandable unit is a mechanical unit which, using electrical energy, is configured to transition from a non-expanded state into an expanded state, or from an expanded state into a non-expanded state, the cable (4) includes lines configured to transfer the required energy from the supply unit (30) to the expandable unit. The sleeve can include internal chambers, configured to enable hydraulic alteration of the volume of at least one of the internal chambers of the sleeve. If the expandable unit is a chamber that can be filled by means of a fluid, the cable (4) includes at least one line allowing the flow of fluid from the supply unit (30) into the chamber. In some implementations, the cable (4) includes at least one pneumatic or hydraulic line. If the device includes one sensor or one electrode at, in or on the sheath, then the line leading to the sensor or the electrode can also be in the cable (4). Embodiments can also exhibit separate cables for providing energy for the expandable unit and for the sensor, or the electrode.

The cable (4) connecting the supply unit (30) to the expandable unit and/or the sensor, or the electrode, can be a single continuous cable or a multi-part cable. In the case of a continuous cable connection, the cable (4) can be attached to the expandable unit and/or the sensor or one electrode. A connector (90) can be attached to the end of the cable (4). The connector (90) can be connected to the supply unit (30) via the matching connector (91). Alternatively, a cable with a connector is only attached to the supply unit (30). In this case, the matching connector is installed on the sheath (2), on the expandable unit and/or on the sensor or electrode. In case of a multi-part cable, a cable (4) with a connector (91) can be attached to the expandable unit and/or at the sensor or the electrode, and a cable can also be attached to the supply unit (30), at the end of which can be a connector. The cable (4) and the connector (90) are described in greater detail in a later section of the description.

Figure 2:
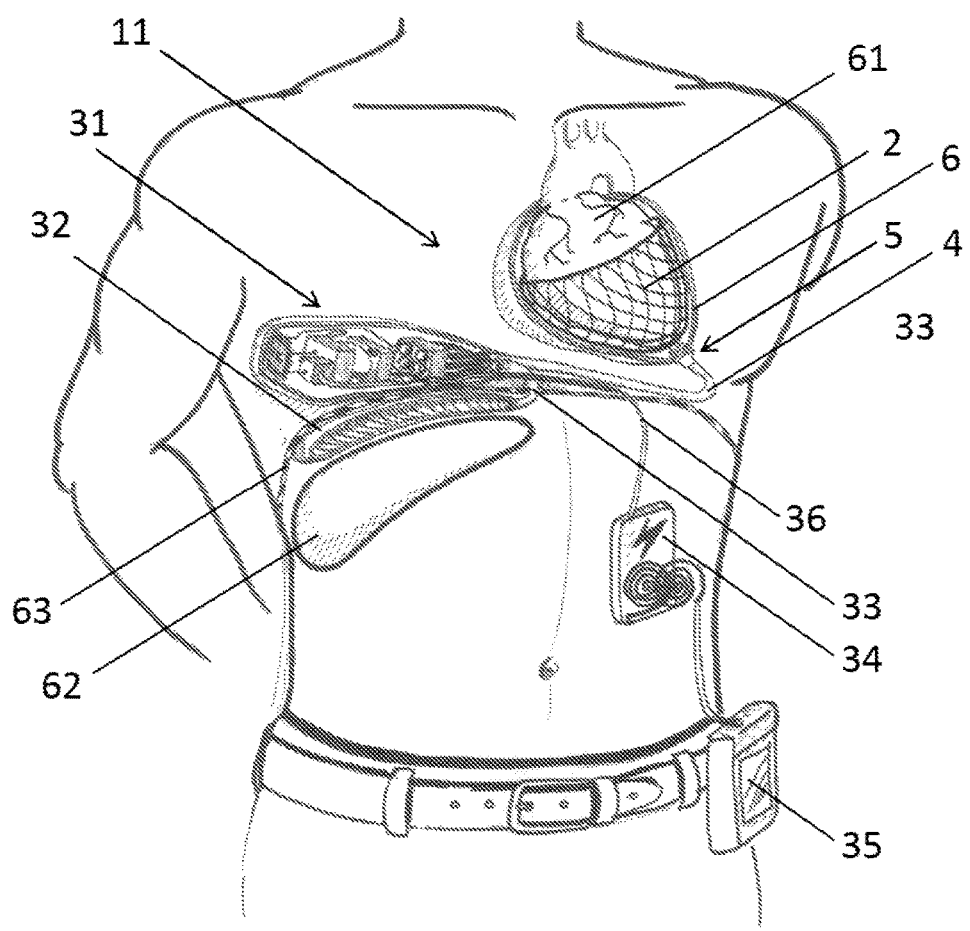
FIG. 2 shows a human torso with an implanted device and a partially implanted supply unit.

FIG. 2 shows an embodiment (11) of the device in the implanted state, where the supply unit (31) is implanted into the body. Preferred locations for the implantation of the supply unit (31) are the chest (thoracic) cavity and the abdominal (peritoneal) cavity, which are separated from each other by the diaphragm (63).

The sheath (2) shown in FIG. 2, the pericardium seal (5), and the cable (4) of the device are essentially identical to the components shown in FIG. 1. The supply unit (31) can include an energy storage device, which can be used to power the expandable unit located inside the sheath (2). The energy storage device can be provided in the form of a rechargeable battery, which supplies electrical energy in order to expand the expandable unit. The supply unit (31) can furthermore contain sensors and one or more microprocessors. If the expandable unit includes at least one chamber, which can be filled with a fluid, then the supply unit (31) can include pumps, valves, and a pressure reservoir. The pressure reservoir can provide a compressed gas in order to inflate an inflatable chamber. Suitable gases are, among others, compressed air, CO2, or inert gases. The housing of the supply unit (31) itself can represent the housing of the pressure reservoir. A preferred place for the implantation of the supply unit (31) is inside the right lateral chest cavity above the liver (62) and above the diaphragm (63). Alternatively, or in addition to the pressure reservoir (32) in the supply unit (31), the pressure reservoir (32) can be preferably implanted inside the right lateral abdominal cavity below the diaphragm (63) and above the liver (62).

The pressure reservoir (32) can be connected to the supply unit (31) with a tube (33), which penetrates the diaphragm (63). The opening in the diaphragm required for the tube (33) to pass through can be sealed with a seal. The seal can be designed similar to the pericardium seal, as previously described. The supply unit can be connected via a cable (4) directly with the expandable unit and/or the sensor, or the electrode. Alternatively, at the end of the cable (4) can also be a connector configured to connect via a matching connector to the supply unit (31) or to the expandable unit and/or to the sensor or the electrode.

The cable (4) runs preferably in the chest cavity above the diaphragm (63). In the case of a multi-part cable, a cable with a connector can be attached to the expandable unit and/or the sensor or one electrode, and a cable with a matching connector can be attached to the supply unit (31).

Alternatively or in addition to a rechargeable battery in the supply unit (31), a rechargeable battery (34) can be implanted subcutaneously, into the abdominal wall. The energy required in the supply unit (31) can be transferred, for example, by electromagnetic induction from an extracorporeal controller (35) transcutaneously to the rechargeable battery (34) and be transmitted by an electric cable (36) from the rechargeable battery (34) to the supply unit (31). The extra-corporeal controller (35) can include an exchangeable rechargeable battery and/or a charging device. The extra-corporeal controller (34) can contain, among others, microprocessors and displays, which can be used for system monitoring of the device and for a display of the operating status. The data from the sensor can be transmitted connectionless via a wireless technology like bluetooth, for example, to and between the supply unit (31) and the controller (34).

Figure 3:
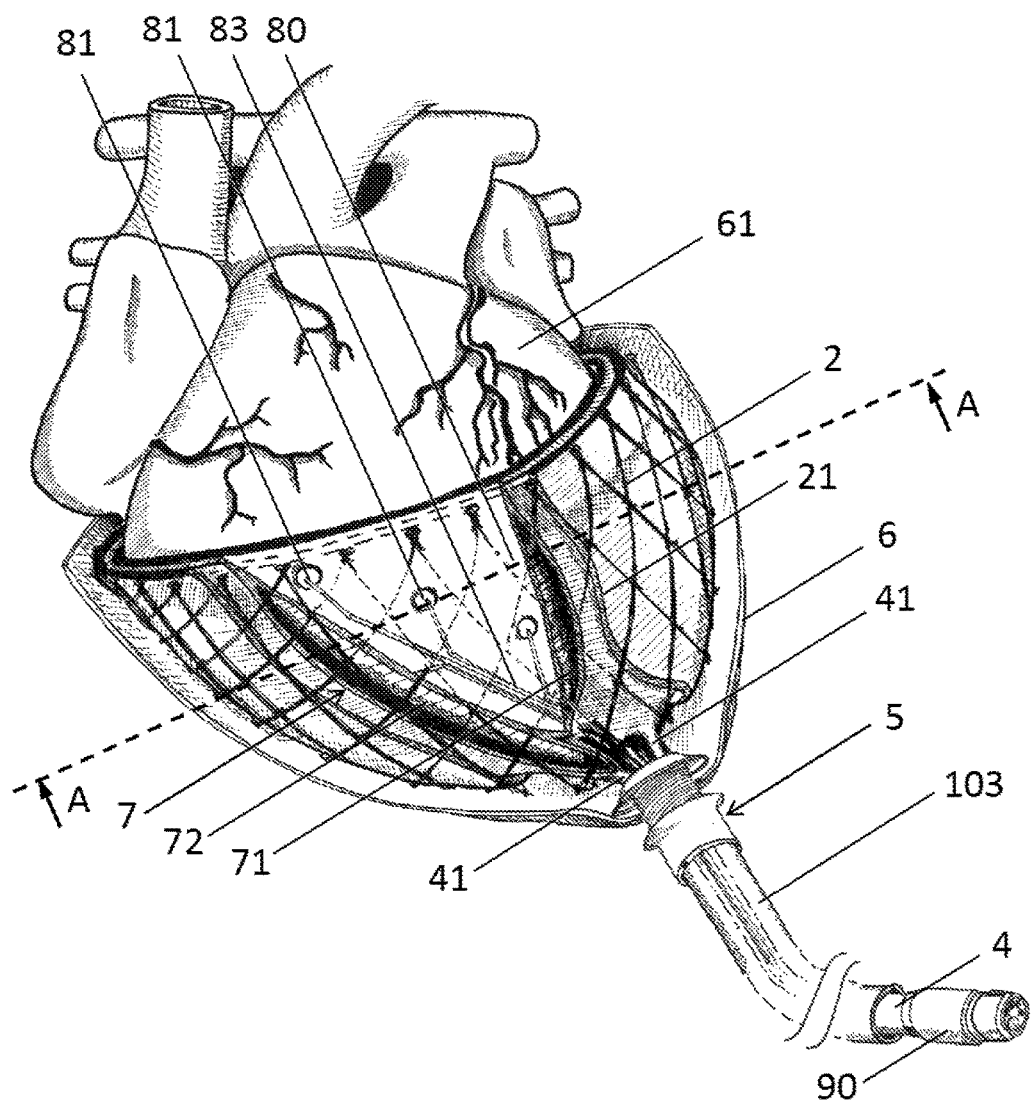
FIG. 3 shows a human heart with the device.

FIG. 3 shows an example of a human heart (61), as well as a sheath (2), a sleeve (7) with expandable units (71, 72), a sleeve (80) with sensors (81) and/or electrodes a cable (4) with a connector (90), a catheter (103) of a delivery system, and a pericardium seal (5) of the device.

In this embodiment, the sheath (2) is shown in the form of a wire mesh. Instead of a wire mesh, the sheath (2) can alternatively be formed as a lattice consisting of links. In this case, the links create a lattice structure with openings. The sheath (2) can also consist of a continuous material, from which parts have been removed; for example, the sheath (2) can consist of a tube and an individually shaped sheath sleeve, into which holes have been formed or cut.

The sheath (2) represented in FIG. 3 consists of a mesh made of wires. The wires form crossing points (intersections), which can be permanently interconnected. The wires could, for example, be welded together at their crossing points. Connecting the wires at crossing points increases the stability of the sheath (2). The crossing points can be free from each other, increasing the flexibility of the sheath (2) and therefore leading to an easier compressibility of the sheath (2). In some embodiments, the sheath includes wires that do not cross each other, forming longitudinally oriented struts. Increased sheath flexibility is especially helpful if the sheath (2) is to be inserted into a delivery system with a smaller diameter catheter (103). Some of the crossing points of the sheath (2) can also be permanently interconnected and others not. Through appropriate selection of crossing points that are permanently interconnected and crossing points that are separable, the stability and flexibility of the sheath (2) can be customized. Areas requiring increased stability in the implanted state can be stabilized by connecting the wires at the crossing points. These can be areas serving as bearing surfaces or abutments for expandable units (71, 72). Such abutments can be located directly under an expandable unit (71, 72) or next to areas with expandable units (71, 72). Areas requiring increased flexibility can be areas which during insertion into a delivery system must be compressed more than other areas. Areas requiring increased flexibility can also be areas, in which an increased flexibility supports the natural movement of the heart. If the sheath (2) is not made of a wire mesh but of a latticework or a sheath sleeve with holes, the stability and/or the flexibility of selected areas of the sheath (2) can be adjusted as well. In these cases, adjustments can be brought about by choosing the width of the links and/or the thickness of the links, through the choice of the material to be used, through modifications of the material in certain areas through application of energetic radiation, like heat, for example. Preferably, the sheath (2) exhibits openings being formed by the wires of a wire mesh, the links of a latticework, or the holes in a sheath sleeve. These openings enable compression of the sheath (2); they allow the exchange of substances from inside the sheath (2) with areas outside the sheath (2) and vice versa; they reduce the amount of material being used for the sheath (2), and they allow an increased flexibility of the sheath (2). Shapes which are difficult to realize with solid materials are easier to achieve with mesh-type or lattice-type structures. The openings can be rectangular, round or oval. The openings defined by the wires, the links or the holes in a sheath sleeve have a diameter of approximately 1 to 50 mm, preferably 4 mm to 10 mm. The diameter of an opening is defined as pin opening, meaning that the diameter of the opening represents the largest diameter of a cylindrical pin that can pass through an opening (e.g., a cell or a hole).

The sheath (2) is preferably made of a material allowing expansion. Preferably, the sheath (2) is formed from a material selected from the group consisting of nitinol, titanium and titanium alloys, tantalum and tantalum alloys, stainless steel, polyamide (PA), polyurethane (PUR), polyether ether ketone (PEEK), polyethylene (PE), polypropylene (PP), polycarbonate (PC), polyethylene terephthalate (PET), polymer fiber materials, carbon fiber materials, aramide fiber materials, glass fiber materials and combinations thereof. A material suitable for forming a self-expanding sheath (2) is at least partially made of a shape memory alloy. Examples of shape memory alloys include NiTi (nickel-titanium; nitinol), NiTiCu (nickel-titanium-copper), CuZn (copper-zinc), CuZnAl (copper-zinc-aluminum), CuAlNi (copper-aluminum-nickel), FeNiAl (iron-nickel-aluminum) and FeMnSi (iron-manganese-silicon).

The sheath (2) preferably exhibits a form adapted to the individual shape of the patient's heart, or a cup-shaped form. The individual shape of the patient's heart can be reconstructed from CT or MRI image data. The sheath (2) is open at the top. The upper rim of the sheath (2) preferably exhibits loops of a wire or straps, which are formed by links. The loops or straps can serve as anchoring points for a sleeve (80) with at least one sensor (81) or one electrode, and/or for a sleeve (7) with at least one expandable unit (71, 72). Positioned at the lower end of the cup-shaped sheath is preferably an opening, through which one or multiple leads of the sensor (81) or of the electrode, and/or of the expandable unit (71, 72) can be passed. The shape of the sheath (2) at least partially represents the anatomical shape of a heart (61), in particular the lower part of a heart (61). Details regarding the shape of the sheath (2) are explained in greater detail in a later section of the description.

The sheath (2) can be covered by a membrane (21), in particular by a membrane (21) made of polyurethane or silicon. The membrane (21) is configured to reduce the mechanical stress applied by the sheath (2) onto the pericardium (6) or the myocardium (61). The membrane (21) can also increase the biocompatibility of the sheath (2). The membrane (21) can be attached to the inner surface or to the outer surface of the sheath (2). The membrane (21) can also be manufactured by dipping the mesh- or lattice-type sheath (2) into an elastomer-containing liquid, which subsequently envelops the latticework or the mesh. The membrane (21) can then stretch across the openings of the mesh or the lattice. A membrane (21) on the mesh or the lattice can also improve the abutment properties of an expandable unit (71, 72). If an expandable unit (71, 72) is, for example, an inflatable chamber, then a membrane (21) across, at or on the mesh or the lattice can prevent parts of the chambers being pressed through the mesh or the lattice while the chamber is expanding. The membrane (21) can furthermore prevent excessive widening of the sheath (2), in particular during inflation of an inflatable chamber. A membrane (21) on a mesh or a lattice can ensure that an expandable unit positioned on the lattice or the mesh expands into a direction from the mesh or lattice towards the inside only. The membrane (21) does not interfere with the compressibility of the sheath (2) while being inserted into a delivery system.

The sheath (2) and/or the membrane (21) can also include an active pharmaceutical ingredient, for example, an anti-thrombotic ingredient, an anti-proliferative ingredient, an anti-inflammatory ingredient, an anti-neoplastic ingredient, an anti-mitotic ingredient, an anti-microbial ingredient, a biofilm synthesis inhibitor, an antibiotics ingredient, an antibody, an anti-coagulating ingredient, a cholesterol-lowering ingredient, a beta blocker, or a combination thereof. Preferably, the ingredient is in the form of a coating on the sheath (2) and/or the membrane (21). The sheath (2) and/or the membrane (21) can also be coated with extra-cellular matrix proteins, in particular fibronectin or collagen. Biocompatible coating can be advantageous if ingrowth of the sheath (2) is desired.

The expandable unit (71, 72) is located inside the sheath (2). FIG. 3 shows a sheath (2), into which a sleeve (7) with expandable units (71, 72) in the form of inflatable chambers is inserted. The expandable unit (71, 72) is being supplied by a line (41) inside the cable (4). The expandable unit (71, 72) can be a hydraulic or a pneumatic chamber. The expandable unit (71, 72) can be attached directly to the sheath (2) without a sleeve (7). The expandable unit (71, 72) can also be attached to a sleeve (7), and the sleeve (7) can be attached inside the sheath (2). The expandable unit (71, 72) can be designed to apply pressure to the heart (61). The applied pressure can be a permanent pressure, or it can be a periodically recurring pressure. The device can include different types of expandable units (71, 72). The device can include at least one augmentation unit (71). The device can include at least one positioning unit (72). The augmentation unit (71) and/or the positioning unit (72) can be attached directly to the sheath (2) or onto a sleeve (7), which is inserted into the sheath (2).

An augmentation unit (71) is a unit that can be periodically expanded and relaxed, and thereby applies a rhythmical pressure to the heart (61). The pressure is preferably applied in the areas of the heart muscle, under which a ventricle is located. By applying pressure on a ventricle by means of the augmentation unit (71) the natural pumping motion of the heart (61) is being amplified or substituted, and the blood inside the heart (61) is pumped from the ventricle into the discharging artery. A pressure applied by an augmentation unit (71) to a right ventricle assists the ejection of the blood from the right ventricular chamber into the pulmonary artery. A pressure applied by an augmentation unit (71) to a left ventricle assists the ejection of the blood from the left ventricular chamber into the aorta. The positioning of the augmentation unit (71) inside the sheath (2) is explained in greater detail in a later section of the description.

A positioning unit is preferably expanded during the operation of the device in support of the heart function more statically than periodically. The positioning unit (72) can be expanded in order to fix the device to the heart and to ensure proper fitting of the device. A positioning device (72) can also be used to respond to changes in the myocardium (e.g., shrinking of the myocardium due to lack of fluids or enlargement of the myocardium due to the absorption of fluids). If the size of the myocardium decreases or increases within a particular period of time, a positioning unit can be expanded or relaxed further in order to ensure a perfect fit. The positioning unit (72) may, for example, also be used to ensure that the device does not lose contact to the heart wall over the span of a heartbeat. Loss of contact can lead to impact stress between the myocardium and the device, and/or cause malfunction of the sensors (81) and/or electrodes. In some implementations, the positioning unit (72) can counteract the pathological, progressive expansion of the damaged myocardium in heart failure patients. The positioning of the positioning unit (72) inside the sheath (2) is explained in greater detail in a later section of the description.

Located at the lower end of the sheath (2) can be an opening, through which the lead (83) from the sensor (81) or the electrode and/or the line (41) of the expandable unit (71, 72) can be passed. The opening can be installed at the lower distal end of the sheath (2). Alternatively, the opening can also be installed on one side of the sheath (2). Shown in FIG. 3 is an opening at the lower distal end of the sheath (2), through which one cable (4), which includes all leads (41, 83), has been routed. Instead of one cable (4), there can be multiple separate cables. The cables can be routed through one opening of the sheath (2) or through multiple openings of the sheath (2). Attached to the end of the cable (4) is a connector (90), which is used to connect the sensor (81) or the electrode, and/or the expandable unit (71, 72) to a supply unit. The sheath (2) is preferably brought inside the pericardium (6). The cable (4) is then passed through the pericardium (6). The device can include a pericardium seal (5). The seal can seal the opening of the pericardium, which is required for the cables to pass through. The pericardium (6) is a connective-tissue-type sac surrounding the heart (61), and which, due to a narrow lubricant layer, gives the heart (61) the ability to move freely. As a lubricant, it contains a serous fluid, also called liquor pericardii. In order to prevent this lubricant from escaping from the pericardium (6) through the cable opening, and to prevent any other fluids or solids (like, for example, cells, proteins, foreign matter, etc.) from entering the pericardium (6), a pericardium seal (5) can be installed around the cable (4). The pericardium seal (5) seals the opening of the pericardium (6) to the cable (4). The pericardium seal (5) can include a first sealing component with a first sealing lip, and a second sealing component with a second sealing lip. A cable (4) can be routed through a central lumen of the seal. The first sealing lip and/or the second sealing lip can seal the pericardium opening. Located inside the central lumen can be an additional sealing component, which seals the cable (4) against the pericardium seal (5) and, if necessary, fixes it as well. The first and the second sealing component can be combined. Preferably, the first and the second sealing component can be secured with a mechanism. Possible mechanisms to secure the sealing components are screw mechanisms, clamping mechanisms, or a bayonet mechanism. The first sealing component and/or the second sealing component can be expandable, or even self-expanding. The pericardium seal (5) is explained in greater detail in a later section of the description.

Figure 4A:
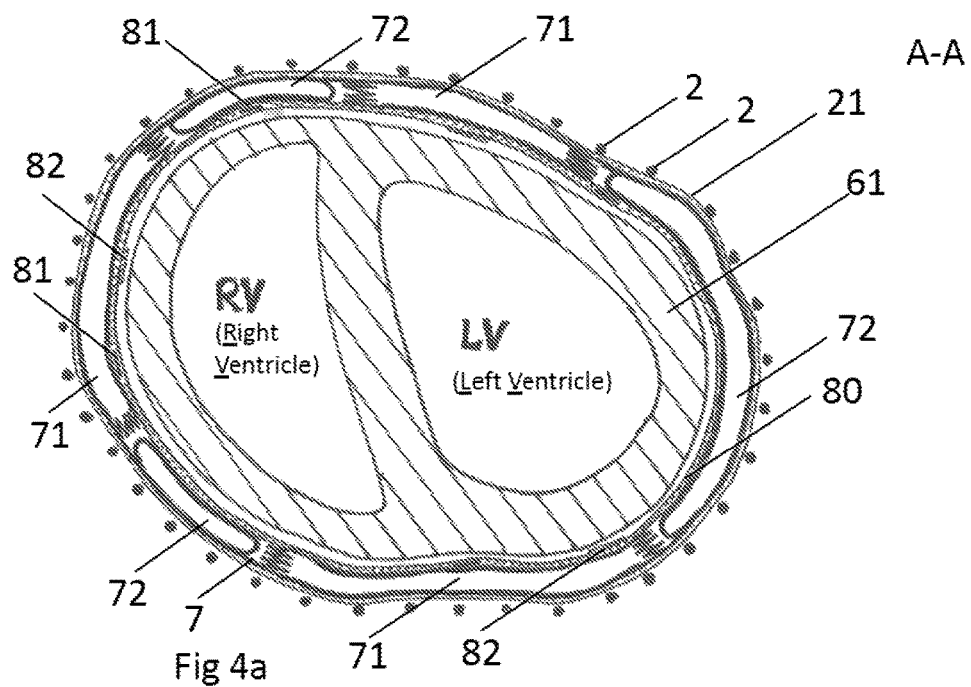
FIGS. 4a and 4b show a cross-section through the heart with the device along line A-A in FIG. 3.
Figure 4B:
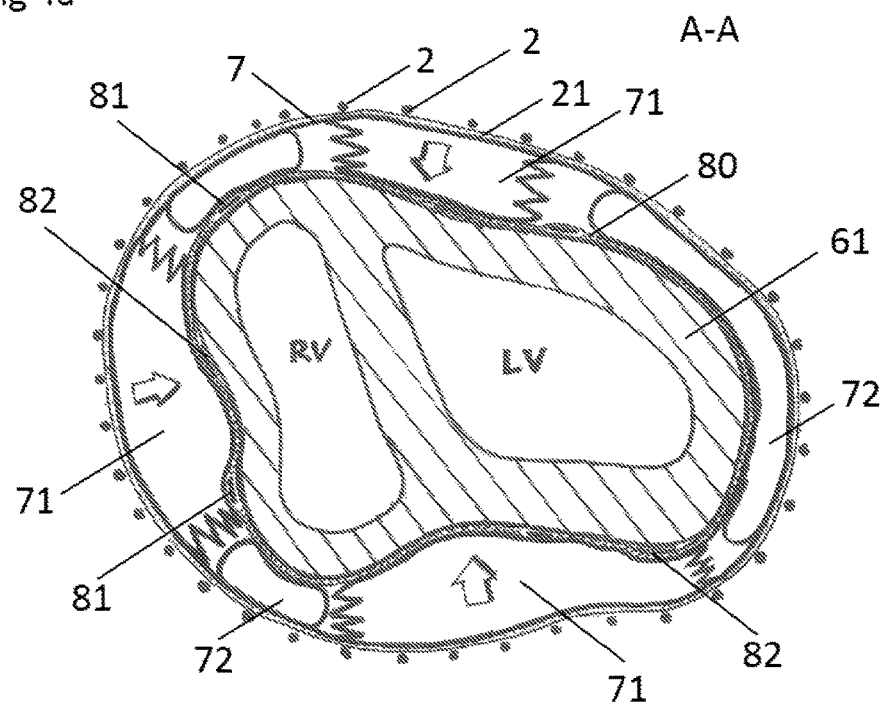

FIGS. 4a and 4b show a cross-section of the heart (61) and part of the device for the support of the cardiac function (61) along line A-A in FIG. 3. Starting from the outside to the inside, the following layers are represented: The sheath (2) with a membrane (21), a sleeve (7) with at least one expandable unit (71, 72), a sleeve (80) with at least one sensor (81) or one electrode (82), and a transverse cross-section of the heart (60). Three augmentation units (71) and three positioning units (72) are illustrated as examples. In FIG. 4a, the expandable units (71, 72) have been drawn in the non-expanded state. In FIG. 4b, the augmentation units (71) have been drawn in the expanded state. The expandable unit (71, 72) is located in an area adjacent to a ventricle. An expansion of the expandable unit (71, 72) can reduce the volume of the ventricle and cause blood to be ejected from the ventricular chamber. The sensor (81) or the electrode (82) is installed in a particular location, where at least one parameter of the heart (61) can be measured. An electrode (82) can be installed in a particular location, where the myocardium can be stimulated. In FIGS. 4a and 4b, four sensors (81) in the sleeve (80) and three electrodes (82) at the inside of the sleeve (80) are illustrated as examples.

Figure 5:
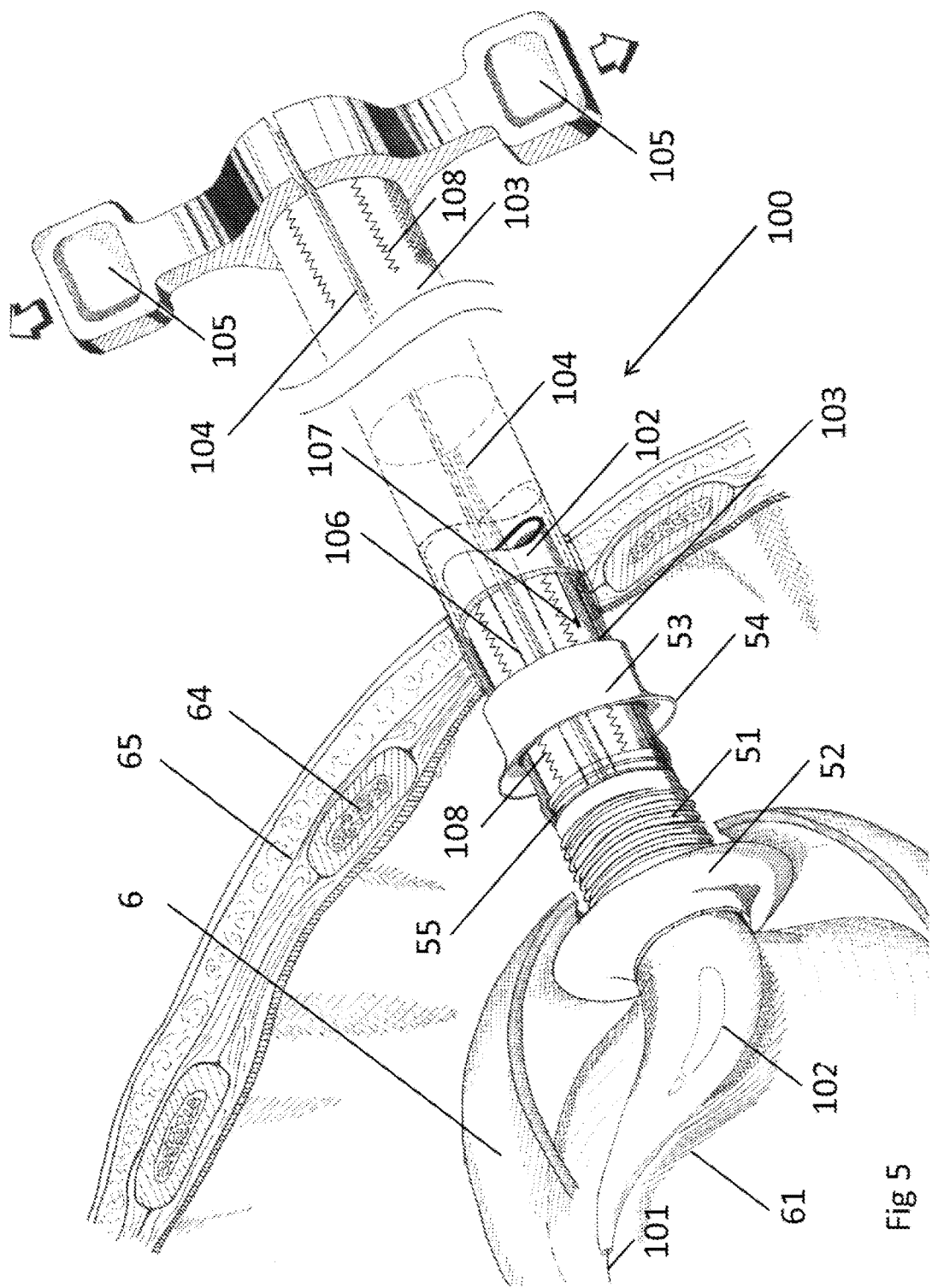
FIG. 5 shows a step of the implantation of the device.

FIG. 5 shows a delivery system (100), which can be used to implant the device to support the cardiac function. The delivery system (100) includes a catheter (103), which has a lumen. Preferably, the catheter (103) is an elongated, tubular component, into which the device for the support of the cardiac function can be inserted in its compressed state. The cross-section of the catheter (103) and/or of the lumen can be circular, oval or polygonal. The delivery system (100) can further include a guide wire (101) and/or a dilatation component. The dilatation component can be soft cone-shaped tip (102) with a shaft. The guide wire (101) can be passed through a puncture of the chest wall (65) between the ribs (64) and of the pericardium (6). The soft, cone-shaped tip (102) can have at the center a circular, oval or polygonal lumen. The soft, cone-shaped tip (102) can be pushed over the guide wire (101) and the puncture can be dilated without injury to the epicardium. The distal section of the catheter (103) of the delivery system (100) can be passed through the dilated opening. At the distal end of the catheter (103), a first sealing component (51, 52) of the pericardium seal can be snapped on or otherwise attached. The catheter (103) may, for example, be pushed onto a cone (55) located at the end of the first sealing component (51, 52). Not shown is another embodiment, where a cone is located at the side of the catheter, onto which the first sealing component can be pushed. The catheter (103) with the attached first sealing component (51, 52) of the pericardium seal can be guided via the shaft of the soft tip (102) and inserted into the pericardium (6).

Alternatively, the catheter (103) and the first sealing component (51, 52) of the pericardium seal can be parts that are not interconnected to each other. In this case, the catheter (103) is initially inserted into the pericardium (6), and the first sealing component (51, 52) can then be pushed into the pericardium via the catheter or withdrawn from the pericardium (6) through the lumen of the catheter (103). The first sealing component (51, 52) can be a self-expanding sealing component, and is configured to unfold inside the pericardium (6). Alternatively, a non-expandable part (51) of the first sealing component contains a self-expanding sealing lip (52) or a sealing lip (52), which is configured to fold down while the first seal component (51, 52) is being inserted, and which opens up inside the pericardium (6). The first sealing component (51, 52) can expand into a mushroom or umbrella-like shape.

A second sealing component (53, 54) can be inserted along the catheter (103) or through the catheter (103). For example, the second sealing component (53, 54) can be moved via the catheter (103) of the delivery system (100) to the distal end of the delivery system (100), and then coupled with the first sealing component (51, 52). The second sealing component (53, 54) can be expandable or non-expandable. The second sealing component (53, 54) can be coupled to the first sealing component (51, 52). The second sealing component (51, 52) is preferably self-expanding, and can in its expanded form assume the shape of a mushroom or an umbrella. The second sealing component (53, 54) can be secured with the first sealing component (51, 52). Shown in FIG. 5 is a screw mechanism. Other mechanisms to secure the sealing components (51, 52, 53, 54) include a clamping mechanism or a bayonet seal. After securing the sealing components (51, 52, 53, 54), the catheter (103) of the delivery system (100) can remain on the cone (55) of the first sealing component (51) or remain in the lumen of the sealing component (51, 52). After the guide wire (101) and the shaft of the soft tip (102) have been pulled out of the catheter, the shell with the sensor or the electrode and/or with the expandable unit can be inserted through the lumen of the catheter (103). The sheath is preferably self-expanding and at least partially encloses the heart (61) after expansion. Located at the lower end of the sheath can be a connector or a cable with a connector. The supply unit can be directly attached to the sheath, or be connected to the sheath via a cable. After the sheath has been delivered, the delivery system (100) can be removed. The delivery system (100) is detached from the sheath by using a pre-weakened breaking point (104) of the delivery system (100) and/or on the catheter (103). Preferably, there are one or multiple pre-weakened breaking points (104) along a longitudinal axis of the delivery system (100). The pre-weakened breaking point (104) can be represented by a breaking line. When the delivery system (100) is broken open along a pre-weakened breaking point (104), the delivery system (100) can be split, unrolled and removed. The delivery system (100) can also include grasping components (105), which can be used to apply a force to the delivery system (100). Preferably, the grasping components (105) can be used to apply a force directed sideways from the catheter (103) onto the delivery system (100) suitable to break open the pre-weakened breaking point (104).

The delivery system (100) can further include a sensor (107). The sensor can be a temperature sensor (107) to measure the temperature within the catheter before and during the implantation of the sheath. The temperature sensor (107) can include a thermocouple, a crystal oscillator or an infrared camera. Alternatively, the sensor can be a sensor to measure at least one of the temperature, pH-value, osmolarity and oxygen saturation of a fluid within the catheter. The wall of the catheter (103) can further contain heating elements (108).

The heating elements (108) can be used to heat the catheter (103) and its content before or during implantation. The delivery system (100) can contain one, two, three, four or more heating elements (108). The heating elements (108) can be arranged along the circumference of the catheter wall (103) equidistantly or irregularly. The heating elements (108) can span the whole length of the catheter (103) or cover the length of the catheter only partially. The heating elements (108) can be adjacent to the catheter wall (103) at the inside or the outside or they can be within the catheter wall.

The heating elements (108) can include heating filaments, heating coils or heating wires, which produce heat via an electrical current. The heating elements (108) can further consist of ducts within the catheter wall that are perfused by a tempered fluid. The catheter can be heated by using a perfusion fluid whose temperature is higher than the ambient temperature. The ducts can also be perfused by a fluid whose temperature is lower than the ambient temperature, in this way the ducts are utilized to cool down the catheter and its content to a lower temperature. With a temperature sensor and the heating elements, the temperature within the catheter can be maintained at a specific level between −5° C. and +40° C.

Figure 6:
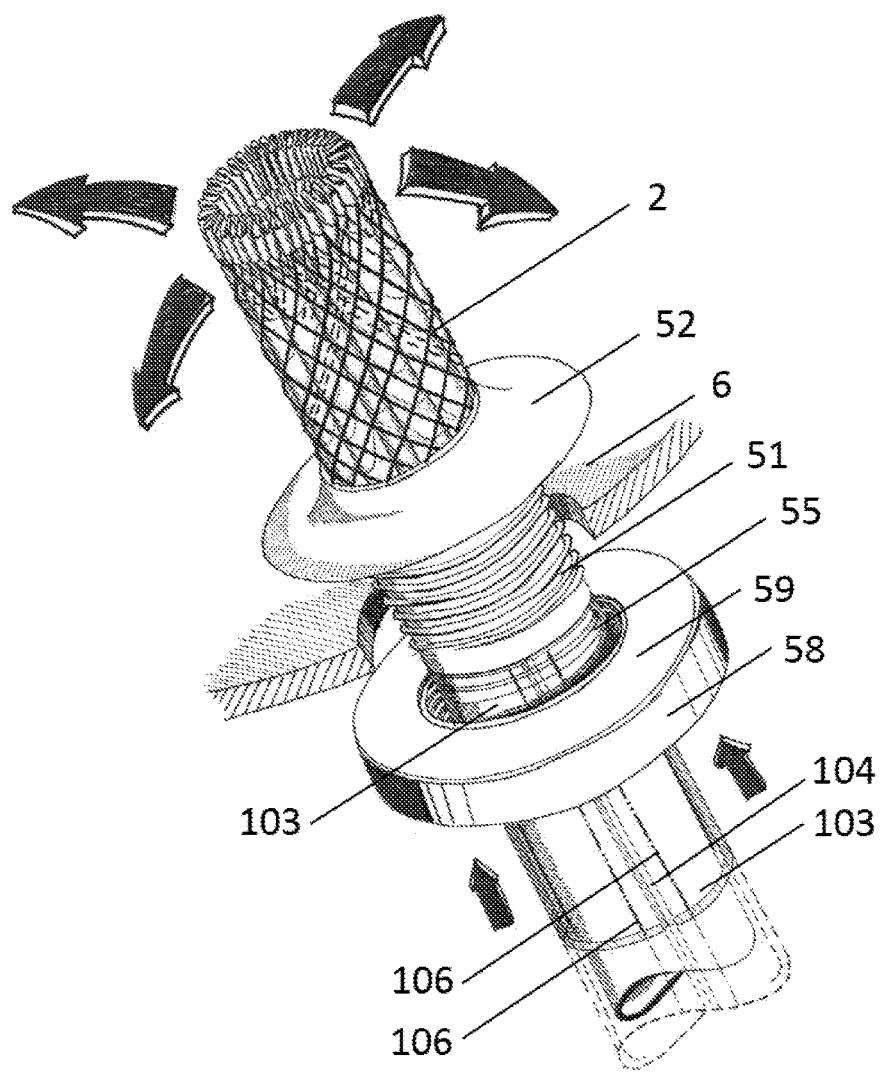
FIG. 6 shows a step of the implantation, in which a pericardium seal has not yet been screwed shut.

FIG. 6 shows a step of the implantation of the device. After the first sealing component (51, 52) in the pericardium (6) has assumed the expanded form, the sheath (2), which is preferably self-expanding, can be passed through the lumen of the catheter (103) of the delivery system and lumen of the first sealing component (51). After entering through the pericardium seal, the sheath (2) with the sensor or the electrode and/or the expandable unit expands inside the pericardium (6).

Shown in FIG. 6 is also the second sealing component (58, 59) before being coupled with the first sealing component (51, 52). In this embodiment, the second sealing component (58, 59) is a ring-shaped component (58), e.g., a nut, on which a sealing disk (59) can be attached to its distal side. The second sealing component (58, 59) can be expandable or non-expandable. The second sealing component (58, 59) can be moved on the catheter (103). In this embodiment, the first sealing component (51, 52) the sheath with the sensor or the electrode and/or with the expandable unit can be inserted through the lumen and the second sealing component (58, 59) exhibit thread sections, which can be screwed together.

Figure 7:
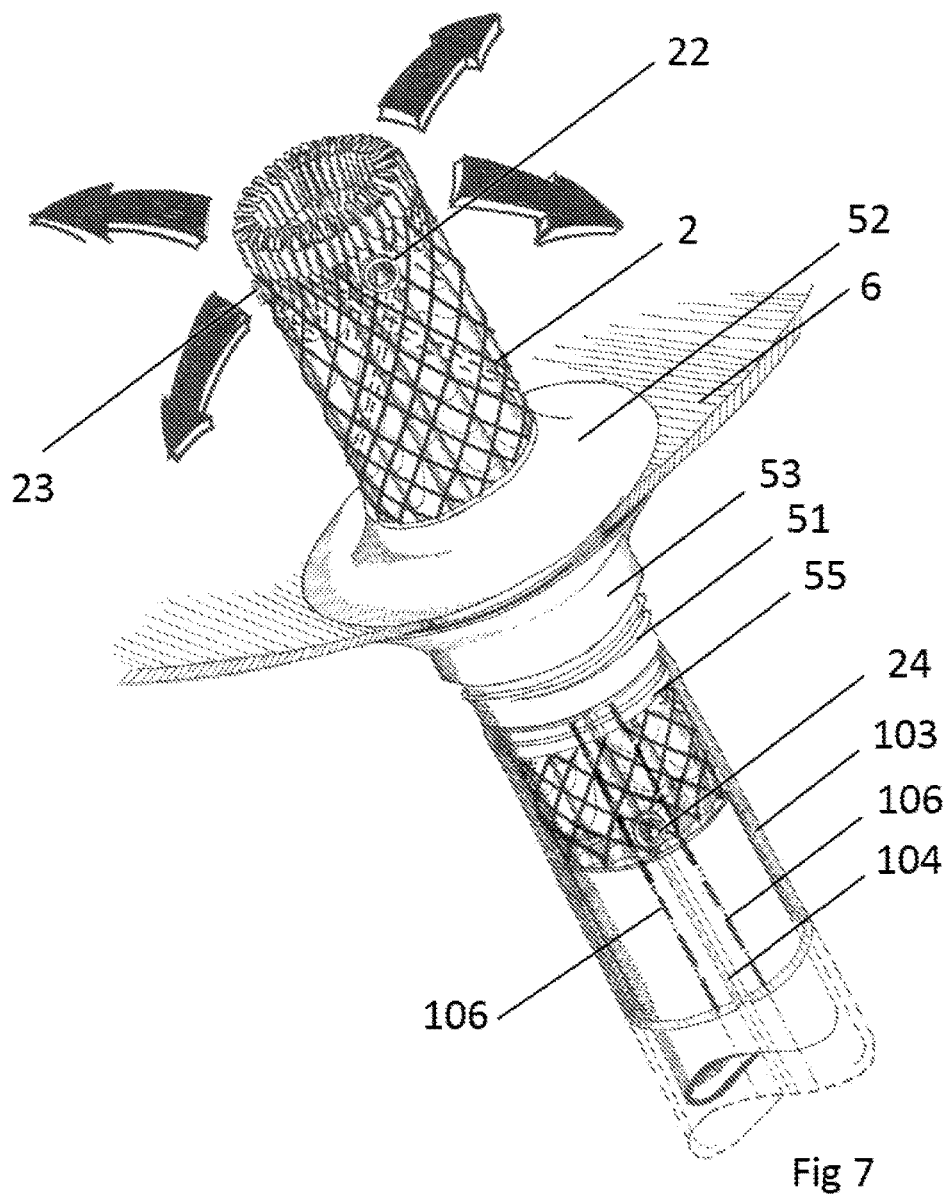
FIG. 7 shows a step of the implantation, in which a pericardium seal is screwed shut.

FIG. 7 shows a step of the implantation of the device. In this embodiment, the first sealing component (51, 52) is coupled with the second sealing component (53). The pericardium (6) can thereby be sealed. The expandable sheath (2) is partially located inside the pericardium (6) and can be expanded. FIG. 7 shows markings (22, 23, 24) applied to the sheath (2). The device generally contains at least one marking (22, 23, 24), which can facilitate the correct placement of the sheath (2). The marking (22, 23, 24) can be a visual mark, in particular a color marking. The marking (22, 23, 24) can be a phosphorescent or fluorescent marking, making it easier to see in dark environment. Such environments can be present in the operating room itself, and can also be caused by the casting of shadows. Such environments can also be inside the body of a patient. The marking (22, 23, 24) can be made of a material able to be represented by imaging techniques. Suitable imaging techniques include X-rays, CT-methods, and MRI-methods. For example, the marking (22, 23, 24) can be formed of a more radiopaque material than the material of adjacent regions. The marking (22, 23, 24) can have the form of a point, a circle, an oval, a polygon, or the form of a letter. Other forms can be areas created by the connecting of dots. The form can be, for example, a half-moon or a star. The marking (22, 23, 24) can be applied to the sheath (2) or applied to a sleeve. The marking can be applied in the form of a line. The line can start at the upper edge of the sheath (2). The line can run from an upper edge of the sheath (2) to a point at the lower tip of the sheath (2). The line can run from the upper edge of the sheath perpendicular to the lower tip of the sheath (2). The starting point of the line at the upper edge of the sheath (2) can be located at a place, which in the implanted state is close to an area, or at an area, which is level with the cardiac septum. The marking (22, 23, 24) can be located at crossing points of the mesh or the lattice. If the sheath (2) includes a sheath sleeve, into which holes were formed, the marking (22, 23, 24) can be worked into the sheath sleeve. For example, a hole can be manufactured with a predefined form, which then serves as marking (22, 23, 24).

The delivery system and/or the catheter (103) of the delivery system can include one or multiple markings (106). A marking (106) on a delivery system can be formed like a marking on a sheath. The marking (106) can have the form of a dot or the form of a line. A marking (106) in the form of a line can be a line, which at least partially describes a circumference of the delivery system. A marking (106) in the form of a line can be a longitudinal line along an axis of the delivery system. A marking (106) in the form of line can be a straight line or a meandering line. A marking (106) in the form of a line can be a line running diagonally on a catheter (103) of a delivery system. A marking (106) can facilitate the orientation of the delivery system during implantation. A marking (106) at or on the delivery system can be in alignment with a line at or on a medical implant. For example, the medical implant can be a device for the support of the cardiac function, which can be compressed. In a compressed state, the device can be inserted into a delivery system. One or multiple markings (22, 23, 24) on or at the device can be aligned with one or multiple markings (106) on or at the delivery system. Such markings (22, 23, 24, 106) facilitate the orientation of a medical implant. Markings (22, 23, 24) can also be located along an axis of a medical implant. Such markings (22, 23, 24) can be helpful in tracking the progress of the discharge of a medical implant out of the delivery system. The delivery system and/or a catheter (103) can be made of a transparent material, which allows the medical implant to be visually traceable during insertion.

Figure 8:
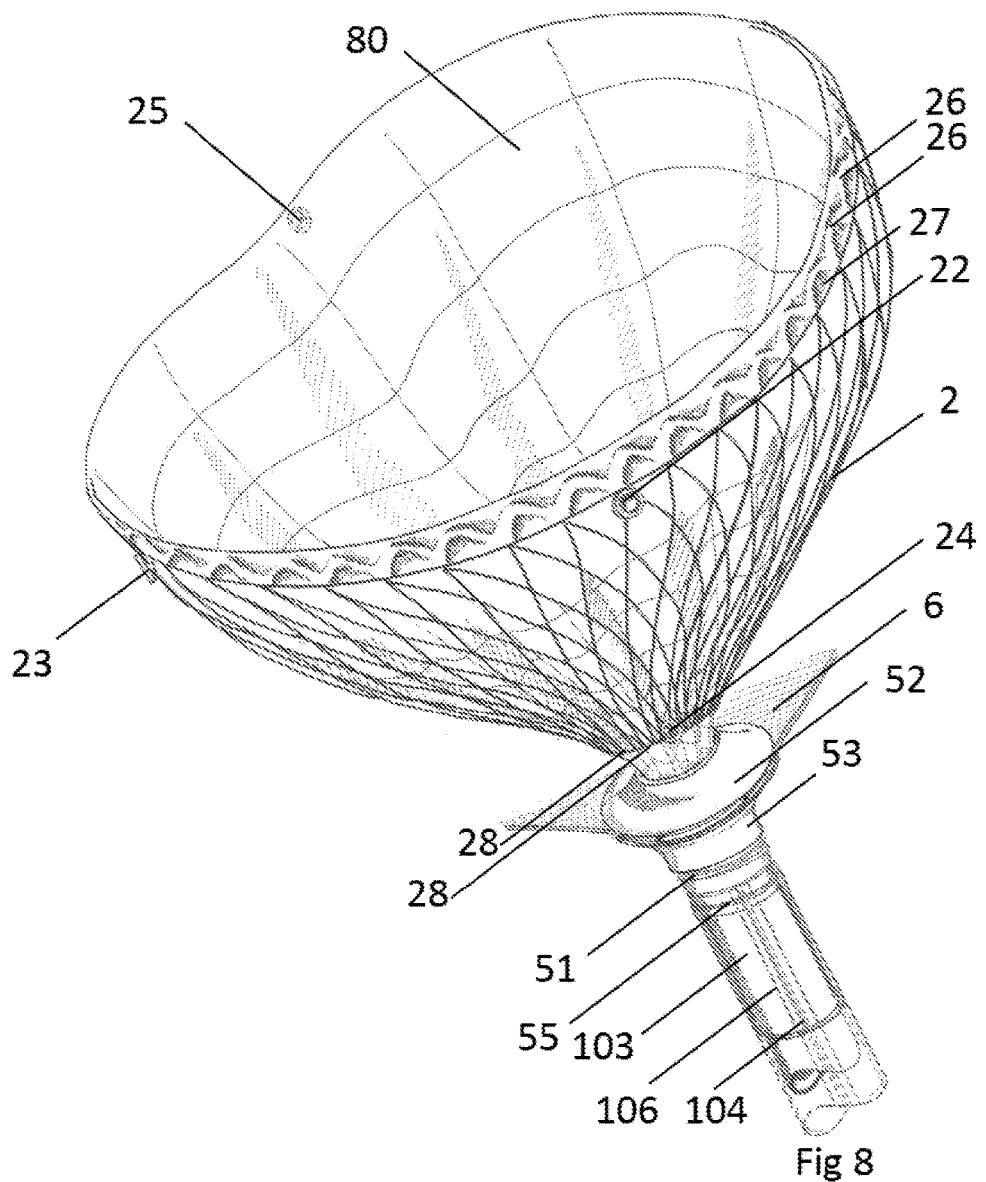
FIG. 8 shows a partially expanded sheath with a sleeve.

FIG. 8 shows a step of the implantation of the device. In this example, the first sealing component (51, 52) and the second sealing component (53) of the pericardium seal are interconnected. The device for the support of the cardiac function has already been partially discharged from the delivery system. Shown is a self-expanding sheath (2). In this embodiment, the sheath (2) is formed from a wire mesh exhibiting loops (26, 28) at the upper edge and/or at the lower edge of the sheath (2). The sheath (2) can also be formed of a lattice structure and can exhibit links in the form of straps at the upper edge and/or at the lower edge of the sheath (2). If the sheath (2) is formed from a sheath sleeve, into which holes have been formed, the upper edge and/or the lower edge of the sheath (2) can be designed such that at least one strap is located at the upper and/or lower edge of the sheath (2). The sheath (2) represented in FIG. 8 includes a sleeve (80), which is inserted into the sheath (2). Another sleeve including at least one expandable unit can be located between the sleeve (80) and the sheath (2).

One or both sleeves can be fastened to the loops (26, 28) or straps of the sheath (2). A sleeve can, in particular, be hooked onto the loops (26, 28) or the straps of the sheath (2). In such case, the sleeve (80) can exhibit at least one pocket (27), which can be pulled over at least one loop (26, 28) or at least one strap. Another embodiment can include a sleeve (80), which is turned inside out at its upper edge and/or at its lower edge. This inversion can form a pocket (27) around the entire sleeve (80) or around a part thereof, which can be hooked into the upper edge and/or the lower edge of the sheath (2). In FIG. 8, the sheath (2) exhibits multiple markings (22, 23, 24, 25). As previously described, these markings (22, 23, 24, 25) can assume different forms or positions. In this case, the markings (22, 23, 24, 25) are attached to the upper edge and the lower tip of the sheath (2).

Figure 9:
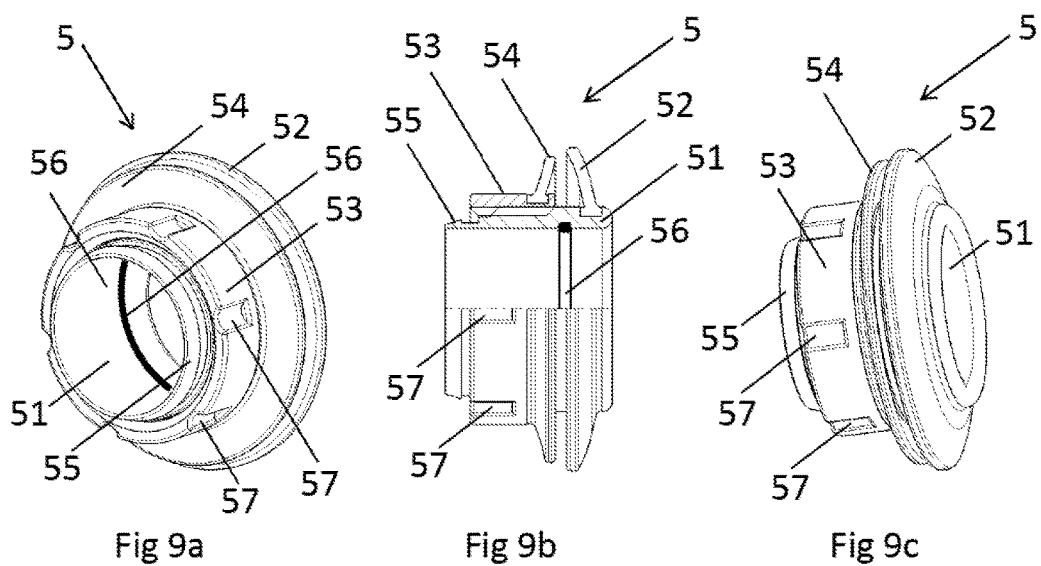
FIGS. 9a-c show different views of a closed pericardium seal.

FIGS. 9a-c show different views of a pericardium seal (5). The pericardium seal (5) serves to prevent the loss of pericardium fluid or also as an option to apply artificial pericardium fluid, medications or other therapeutics. The prevention of loss of pericardium fluid also serves to prevent adhesions of the system with the epicardium. The pericardium seal (5) generally includes a first sealing component (51) and a second sealing component (52). The first sealing component (51) has a central lumen, and the second sealing component (53) has a central lumen. The first sealing component (51) can be coupled with the second sealing component (53). After coupling the first sealing component (51) to the second sealing component (52), the pericardium seal (5) exhibits a lumen running through the pericardium seal (5). The lumen can be formed exclusively by the central lumen of the first sealing component (51), or the lumen can be formed exclusively by the central lumen of the second sealing component (53). In another embodiment, the lumen can also be formed from both lumens of the two coupled sealing components (51, 53). Located in the lumen can be a sealing gasket, an O-ring, a labyrinth seal or another sealing component (56). A sealing component (56) in the lumen of the pericardium seal can seal the pericardium seal (5) against an object protruding through the pericardium seal (5). For example, a cable can be passed through the pericardium seal (5), which is then sealed against the pericardium seal (5). A sealing component (56) in the lumen can serve not only to seal but also to fix an object protruding through the lumen of the pericardium seal. The sealing component (56) can be attached to both sealing components (51, 53) or to one of both sealing components (51, 53) only.

Using a mechanism, the first sealing component (51) can be secured with the second sealing component (53). A mechanism to secure a first sealing component (51) with a second sealing component (53) can include a screw mechanism or clamping mechanism. A mechanism to secure a first sealing component (51) with a second sealing component (53) can also include a bayonet catch. The first sealing component (51) and the second sealing component (53) can be made of the same material or made of different materials. Suitable materials for the first sealing component (51) and/or the second sealing component (53) include synthetic materials, metals, ceramics or combinations thereof.

Attached to the first sealing component (51) can be a first sealing lip (52). The first sealing lip (52) can be part of the first sealing component (51) or can be attached to the first sealing component (51). Attached to the second sealing component (53) can be a second sealing lip (54). The second sealing lip (54) can be part of the second sealing component (53) or can be attached to the second sealing component (53). The first sealing lip (52) and the second sealing lip (54) can be formed of the same material or of different materials. One or both sealing lips (52, 54) can be part of the respective sealing component (51, 53) and can be formed from the same material as the associated sealing component (51, 53). The first sealing lip (52) and/or the second sealing lip (54) can be formed of a synthetic material (preferably of an elastomer), natural rubber, rubber, silicon, latex or a combination thereof. The first sealing lip (52) and/or the second sealing lip (54) can be disk-shaped. The first sealing lip (52) and/or the second sealing lip (54) can exhibit a concave or a convex curvature. Curved sealing lips (52, 54) can better adapt to anatomic conditions. The pericardium exhibits a convex form in the area of the cardiac apex. With the sealing lips (52, 54) exhibiting a curvature in the shape of the anatomically available form, an improved anatomic fit of the pericardium seal (5) can be achieved.

Curved sealing lips (52, 54) can also be used to achieve better sealing properties. The first sealing lip (52) and/or the second sealing lip (54) can have reinforcements. With increasing radial distance from the lumen of the pericardium seal towards the outside, the first sealing lip (52) and/or the second sealing lip (54) can exhibit increased flexibility. Increased flexibility at the edges of sealing lip (52, 54) can strengthen the sealing properties of the sealing lip (52, 54) and can also support the anatomically correct positioning of the sealing lip (52, 54). Increased flexibility at the edges of the sealing lip (52, 54) can be achieved through the choice of material. Each sealing lip (52, 54) can be made of one material or of multiple materials. Reinforcements of a sealing lip (52, 54) can be concentric reinforcements or radial reinforcements. Reinforcements can be achieved by means of variable material thicknesses or by introduction of a reinforcing material. The reinforcing material can be the same material as the base material of the sealing lip (52, 54), having been converted into a different form of the material. Alternatively, regions, that are not to be reinforced can be weakened by converting the material of the sealing lip (52, 54) into a weaker form of the material. A weakening of the material can be induced by exposure to energetic radiation (e.g., heat). Reinforcements of the material can also be achieved by application of material, whereby the applied material can be the same material as the base material of the sealing lip (52, 54), or whereby the applied material can be a material different from the base material of the sealing lip (52, 54). Suitable materials for the reinforcement of sections of a sealing lip (52, 54) are metals, ceramics, rubber, or a combination thereof.

One of the two sealing components (51, 53) can exhibit a coupling mechanism, allowing the coupling of a sealing component (51, 53) with the delivery system or a catheter of the delivery system. The coupling mechanism can consist, for example, of a cone (55) located at the first sealing component (51), onto which the delivery system or a catheter of a delivery system can be clamped. The clamping effect can be achieved by the diameter of the cone (55) being larger than the luminal diameter of the delivery system, for example. The coupling mechanism to couple the pericardium seal (5) to the delivery system can also be available at the second sealing component (53). The coupling mechanism can also be provided as a separate part in addition to the sealing components (51, 53), and can link the delivery system to one of the two sealing components (51, 53) of the pericardium seal (5). Other embodiments of the coupling mechanism may include, among others, a non-conical (e.g., cylindrical) extension on one of the sealing components (51, 53), onto which the delivery system can be placed or glued. In some embodiments, the catheter of the delivery system and a sealing component form a single integrated part. In some embodiments, the catheter can after successful insertion and securing of the pericardium seal (5) be disconnected from the sealing component (51, 53) or the pericardium seal (5) by means of a pre-weakened breaking point.

One or both sealing components (51, 53) can exhibit engaging components (57). These engaging components (57) can be used to apply a force to one or both sealing components (51, 53) appropriate to couple and/or secure the sealing components (51, 53). Engaging components (57) on one or on both sealing components (51, 53) can be holes, indentations or elevations. The engaging components (57) can be installed around the circumference of the sealing component (51, 53) at an equal distance from each other. The circumferential distance between the engaging components (57) can also vary. FIGS. 9*a-c* illustrate six engaging components (57) equidistantly disposed around the circumference. On the ring-shaped sealing component (53), the six engaging components (57) are installed at an angular distance of approximately 60°. In the case of two, three, four, five, six, eight or more evenly distributed engaging components (57), the angular distance is 180°, 120°, 90°, 72°, 60°, 45° or less, respectively. The engaging components (57) can also be installed in an unevenly spaced configuration.

Figure 10:
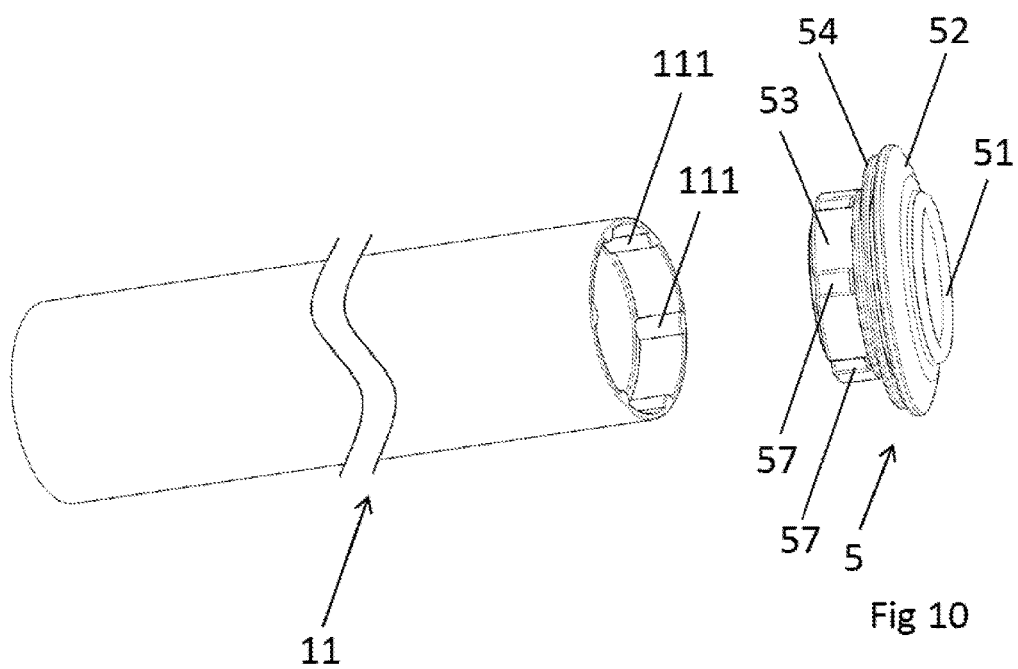
FIG. 10 shows a tool for the closing of a pericardium seal.

FIG. 10 shows a pericardium seal (5) and a tool (11) to secure a pericardium seal (5). The pericardium seal (5) shown in FIG. 10 is essentially identical to the seal shown in FIG. 9. As an example, the tool (11) is represented as an elongated tubular tool. Located at the distal end of the tool (11) are components (111), which can be at least partially engaged with the engaging components (57) of a sealing component (53). In the embodiment shown in FIG. 10, the inside of the tubular tool (11) exhibits at the distal end six elevations (111) pointing to the inside, which can engage with the six engaging components (57) of the sealing component (53), for example, with six indentations on the sealing component (53). The tool (11) essentially exhibits the same number of components (11), which are complementary to the engaging components (57) of the sealing component (53). The tool (11) shown in FIG. 10 is a tubular tool, consisting of a complete tube. The tubular component of the tool (11) can also be half a tube, a quarter tube, or a third of a tube. In the extreme case, instead of the tube, only one shaft or multiple shafts can be attached to a distal, ring-shaped tool. A shaft can extend from the ring-shaped tool in longitudinal direction. A shaft can also extend laterally away from a longitudinal axis of the tool. Other embodiments of the tool (11) (not shown) can be provided in the form of a modified box wrench or a modified open-end wrench.

Figure 11:
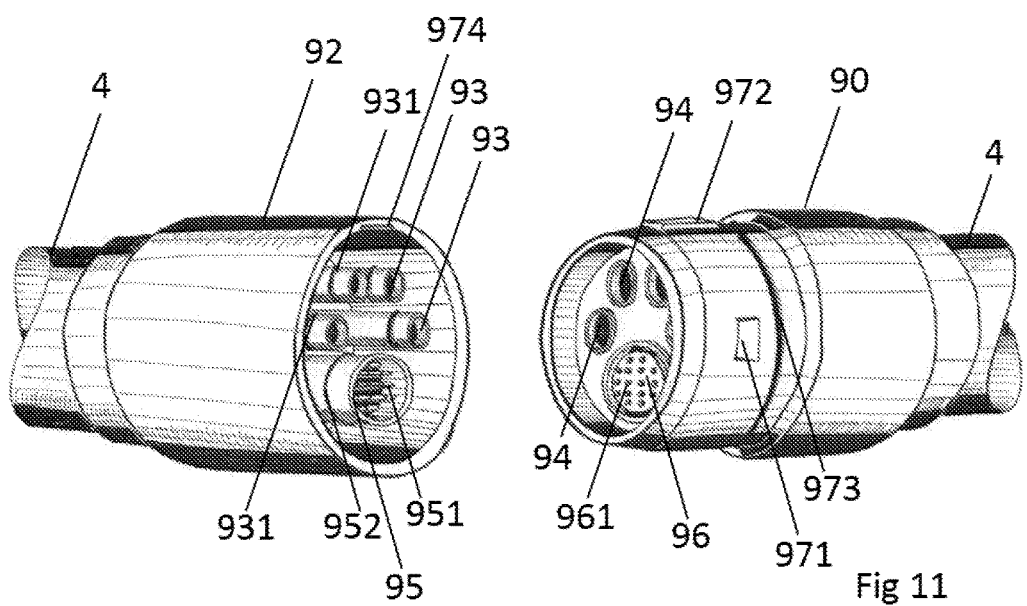
FIG. 11 shows a plug connector system of the device.

FIG. 11 shows a connector system consisting of two connectors (90, 92). The device for the support of the cardiac function includes a sheath with at least one sensor or at least one electrode and/or at least one expandable unit, whereby the sensor or electrode and/or the expandable unit are connected to a supply unit. The sensor or the electrode and/or the expandable unit can be directly connected to the supply unit. The sensor or the electrode and/or the expandable unit can be connected to the supply unit via a cable (4). The sensor or the electrode and/or the expandable unit can be directly linked to the supply unit via the cable (4), or the sensor or the electrode and/or the expandable unit can be connected to the supply unit. The supply unit can include a connector (92). The connector (92) can be attached directly to the supply unit. The connector (92) can be connected to the supply unit via a cable (4). The sensor or the electrode and/or the expandable unit can include a cable (4). At the end of the cable (4) can be a connector (90). The connector (90) at the end of the cable of the sensor or of the expandable unit matches the connector (92) at the supply unit. The connector (90) of the sensor or of the electrode and/or the expandable unit can be a male or a female connector. A female connector on the side of the sensor or the electrode and/or the expandable unit can be advantageous, since the female connector in contrast to the male connector does not include any pins (951) or any other terminals, which can protrude and therefore could break. If an exchange of the supply unit is required, the connector system is disconnected, and a new supply unit is connected to the connector (90) of the sensor or the electrode and/or the at least expandable unit. The reconnection of the connector (90) with a supply unit might cause pins (951) or other terminals to break. If the pins (951) or terminals are located in a male connector on the side of the sheath with the sensor or the at last one electrode and/or the expandable unit, an exchange of the sheath may be required. A female connector on the side of the sheath with the sensor or the electrode and/or the expandable unit can be advantageous, since the breaking of pins (951) or other terminals cannot occur at a female connector. The connector system (90, 92) usually includes two connectors. The device can consist of a connector system (90, 92) for the sensor or the electrode and/or the expandable unit, or of multiple connector systems. If multiple connector systems are used, a connector system for electrical leads and a connector system for hydraulic and/or pneumatic lines can be provided. The connector system (90, 92) represented in FIG. 11 is a connector system consisting of connections to supply the sensor or the electrode and the expandable unit. The number of connections depends on how many sensors or electrodes and how many expandable units are being used. In some implementations, the number does not necessarily have to correlate directly with the number of sensors or electrodes and/or the number of expandable units. Split leads/lines on both sides of the connector system (90, 92) are possible, and a pneumatic or hydraulic line is configured to supply one, two, three, four, five, six or more fillable chambers. The filling of the multiple chambers by one line does not have to occur simultaneously; it can also occur individually by means of individually controllable valves. Likewise, one electrical lead inside the cable can be used for multiple sensors or electrodes, and switches can individually energize circuits. The connector system (90, 92) represented in FIG. 11 includes four hydraulic or pneumatic connection ports (93, 94) and one connection for electrical leads (95, 96). The connecting port for electrical leads (95, 96) shown in FIG. 11 exhibits 16 connecting components in the form of pins (951) and pin sockets (961). More or fewer connections for electrical leads (95, 96) and/or pneumatic or hydraulic lines (93, 94) can exist in one connector system. The pneumatic or hydraulic lines (93, 94) can include one, two, three, four, five, six, seven, eight, nine or ten connections.

The electric leads (95, 96) can include one, two, three, four, five, six, seven, eight, nine, ten, twelve, fourteen, sixteen, twenty or more connections. One electrical connector for electric leads (95, 96) can have one, two, three, four, five, six, seven, eight, nine, ten, twelve, fourteen, sixteen, twenty or more connecting components in the form of pins (951) and pin sockets (961). The number of connecting components in the form of pins (951) and pin sockets (961), however, is identical for the respective pair of connections for electricals leads (95, 96). Each of the connections (93, 94, 95, 96) in one or in both of the connectors of the connector systems (90, 92) can have its own seal (931, 952). The seal (931, 952) of the individual connections (93, 94, 95, 96) can be a sealing tape or a sealing gasket. The connector system (90, 92) can in addition or only one seal inside the connector system (973) or around the connector system. A seal via the connector system can be a sealing tape or a sealing gasket. The connector parts (90, 92) can be interconnected in order to create the connector system (90, 92). The connector parts (90, 92) can have a guide peg (972) and a guide slot (974). The guide peg (972) and the guide slot (974) can prevent wrong connection of the two connector parts and/or turning the connector parts the wrong way during connection. The connector parts (90, 92) can also include two, three, or more guide pegs (972) and guide slots (974). In the case of two or more guide pegs (972) and guide slots (974), unequal distances between the individual guide pegs (972) and guide slots (974) can be used. The interconnected connector parts (90, 92) can also be secured with a mechanism (971). Such mechanism (971) can be a screwing mechanism or a clamping mechanism or a bayonet catch. A mechanism to secure the interconnected connector system (90, 92) can also be a retainer nut, a clamp, a latch or a snap-lock mechanism. Securing the connector system (90, 92) is advantageous, since any accidental partial or complete disconnection of the connector system (90, 92) can interrupt the supply of the sensor or the at least one electrode and/or the expandable unit.

FIG. 12 shows a model for the preparation of a system of coordinates. The development of a system of coordinates can facilitate the manufacture of a device for the support of the cardiac function, since the position for the sensor or one electrode and/or the expandable unit and/or the marking can be exactly defined. FIG. 12a shows a heart (61) with anatomical points of reference. The example illustrates the heart (61) with the aortic arch (AO) originating at the left ventricle (LV) (with head arteries, neck arteries, and subclavian arteries (TR, CL, SCL) branching off), and the pulmonary artery (PU) originating at the right ventricle (RV). Also shown are sections of the inferior vena cava (IVC) and the superior vena cava (SVC). The broken line (601) represents the height of the valve plane. The point (604) of the cardiac apex is defined by letting a perpendicular (603) fall from this plane (601) through the most distal point of the cardiac apex. The device includes a sheath, into which a sleeve with at least one sensor or one electrode and/or a sleeve with at least one expandable unit can be inserted. The dimension of the sheath and/or the sleeve can be designed such that the upper edge of the sleeve (602) runs parallel to the valve plane with a downward offset in the direction of the cardiac apex at a distance from the valve plane of 1 mm to 30 mm, 3 mm to 20 mm, 5 mm to 10 mm, preferably 5 mm. The upper edge of the sheath is shown by the line (602) in FIG. 12a. The lower edge of the sheath (605) and/or the sleeve can be parallel to the valve plane with a distance to the most distal point (604) of 1 mm to 30 mm, 3 mm to 20 mm, 5 mm to 10 mm, preferably 5 mm. FIG. 12b shows a cutting plane B-B along the line (602) shown in FIG. 12a, i.e., along the line corresponding to the upper edge of the sheath.

FIG. 12b shows the right ventricular chamber (RV) and the left ventricular chamber (LV), the heart wall and the septal wall separating the cardiac chambers. The points (608) and (609) are defined as the points of intersection of the centerlines of the heart wall with the septal wall. The point (608) is also called the anterior intersecting point of the centerlines of the heart wall with the septal wall. The point (609) is also called the posterior intersecting point of the centerlines of the heart wall with the septal wall. The center point on a line connecting points (608) and (609) is defined as point (607). These points can be used to define a system of polar coordinates. The z-axis (606) of the polar coordinate system is defined as the line connecting the most distal point (604) to the center point (607) of the line connecting points (608) and (609). The circumferential direction of the coordinate system is suggested by the reference numeral (610) and defined as angle measure $\varphi$, whereby a line radially running from the z-axis (606) through the anterior point of intersection (608) is defined as $\varphi=0°$.

FIG. 13 shows a sheath and/or sleeve with the coordinate system described above in conjunction with FIG. 12. FIG. 13a shows a 3D-model (611) of a sheath or sleeve with the z-axis (606) extending through the most distal point (604) and the center point (607) of the line connecting points (608) with (609). The points (608) and (609) are the anterior and the posterior point of intersection of the center lines of the heart wall with the septal wall, whereby the $\varphi=0°$ line is drawn through the point (608). The broken line connecting the points (608) and (609) along an outer circumference of the sheath or the sleeve, represents the position of the septal wall of the heart as projected onto the sheath/sleeve. At the upper edge of the sheath or the sleeve, the angle measures starting at $\varphi=0°$ are shown in 30° increments, whereby—viewed from above—the angles increase counterclockwise. Longitudinal lines (613) projected onto the sheath/sleeve respectively extend along these angles up to the cardiac apex (604). The angle measure of $\varphi=360°$ then again corresponds to the angle measure of $\varphi=0°$. Contour lines (614) are indicated at distances of 15 mm increments. The contour lines (614) and planes are running perpendicular to the z-axis (606). The broken-dotted line (615) constitutes a cutting line, where the 3D shape (611) can be cut open and rolled out. FIG. 13b shows a rolled-out sheath or sleeve (612), which has been cut along the line (615) in FIG. 13a and then rolled out. The positions (608, 609) and lines (613, 614, 615, 616) shown in FIG. 13b represent the same positions and lines that are shown in FIG. 13a.

FIG. 14 shows a sleeve (7) with at least one expandable unit (71, 72). The 3D-shape of the sleeve (7) in FIG. 14a is comparable to the 3D-model explained in conjunction with FIG. 13a and shows a coordinate system as described above. The sleeve (7) can at least partially enclose a heart. The sleeve (7) can at least partially have the shape of a heart. The sleeve (7) can have a shape similar to the sheath. The sleeve can be inserted into the sheath. The sleeve can be made of synthetic material, polymer, natural rubber, rubber, latex, silicon or polyurethane.

In FIG. 14a, the sleeve (7) with at least one expandable unit (71, 72) is shown as a sleeve (7) with a multiplicity of chambers. FIG. 14b shows a 2D-rollout of the 3D-model from FIG. 14a. The rollout represented in FIG. 14b is essentially identical to the rollout of a 3D-model explained in conjunction with FIG. 13b. Unlike in FIG. 13a, the 3D-model in FIG. 14a is rotated such that a view from above into the sleeve (7) is possible. In FIGS. 14a and 14b, four expandable units (71, 72) are shown as examples, three of which are augmentation units (71) and one is a positioning unit (72). The expandable units (71, 72) can be structurally similar but can serve different purposes, as described above.

Generally, an augmentation unit (71) can be periodically expanded and relaxed in order to be configured to apply pressure to the heart. This pressure is preferably applied in ventricular areas. By applying pressure to a ventricle via the augmentation unit (71) the natural pumping motion of the heart is supported or substituted, and the blood inside the ventricular chamber is pumped into the corresponding artery. A pressure applied by an augmentation unit (71) to a right ventricle leads to the blood being ejected from the right ventricle into the pulmonary artery. A pressure applied by an augmentation unit (71) to a left ventricle leads to the blood being ejected from the left ventricle into the aorta.

FIG. 14 shows three augmentation units (71), which are located at the upper edge of the sleeve (7). In this example, each of the augmentation units (71) is supplied by its own line (41).

In the case of augmentation units (71) in the form of inflatable chamber, the lines (41) are preferably pneumatic or hydraulic lines. Other embodiments include one, two, three, four, five, six or more augmentation units (71), which are supplied by one, two, three, four, five, six or more lines (41). The line (41) can be made of synthetic material, polymer, natural rubber, rubber, latex, silicon, or polyurethane. The line (41) can run above, adjacent to or below the augmentation unit (71). The line (41) can preferably run below a positioning unit (72), so that no pressure points result between the line (41) and the heart wall. The line (41) can also run above or adjacent to a positioning unit (72).

The augmentation units (71) A1, A2, and A3 shown in FIG. 14 are located in an area at the upper edge of the sleeve (7) and are each supplied by their own respective line (41). The augmentation units (71) A1 and A2 can—as illustrated in FIG. 14—be positioned such that they can assist a left ventricle. Augmentation unit (71) A3 is positioned to assist a right ventricle. The individual augmentation units (71) A1, A2 and A3 can be expanded individually. Augmentation units (71) A1 and A2 can assist cardiac function for a heart with left ventricular insufficiency. Augmentation unit (71) A3 can serve to support a right ventricular insufficiency.

Augmentation units (71) A1, A2 and A3 can be used for support of a bilateral heart insufficiency. The augmentation units (71) can be expanded synchronously or asynchronously. Preferably, the expansion of the augmentation units (71) can be coordinated such that a natural pumping function of the heart is supported.

A positioning unit (72) is a unit, which can also be expanded. Preferably, a positioning unit is expanded during operation of the device for the support of the cardiac function more statically than periodically. The positioning unit (72) can be expanded in order to fix the device to the heart and to optimize the accuracy of the fit of the device. A positioning unit (72) can also help to respond to changes of the myocardium. If the size of the myocardium decreases or increases, a positioning unit can be expanded or relaxed further in order to ensure a perfect fit.

FIG. 14 illustrates a positioning unit (72), which essentially fills the spaces between the three augmentation units (71) on the sleeve (7). The positioning unit (72) can have a distance from one or multiple augmentation units (71) of 1 mm, 3 mm, 5 mm, 10 mm, 20 mm, 30 mm, 40 mm or more. The positioning unit (72) can be supplied by its own line (41), in the case of a chamber fillable with a fluid, by a pneumatic or hydraulic line. Other embodiments include one, two, three, four, five, six or more positioning units (72), which are supplied by one, two, three, four, five, six or more pneumatic or hydraulic lines (41). The line (41) can consist of a synthetic material, polymer, natural rubber, rubber, latex, silicon or polyurethane. The line (41) for the supplying of the positioning unit (72) can run below the positioning unit (72). The positioning unit (72), shown in FIG. 14, fills the spaces between the augmentation units (71). The depicted positioning unit (72) has extensions that protrude into the spaces between the augmentation units (71).

Figure 15A:
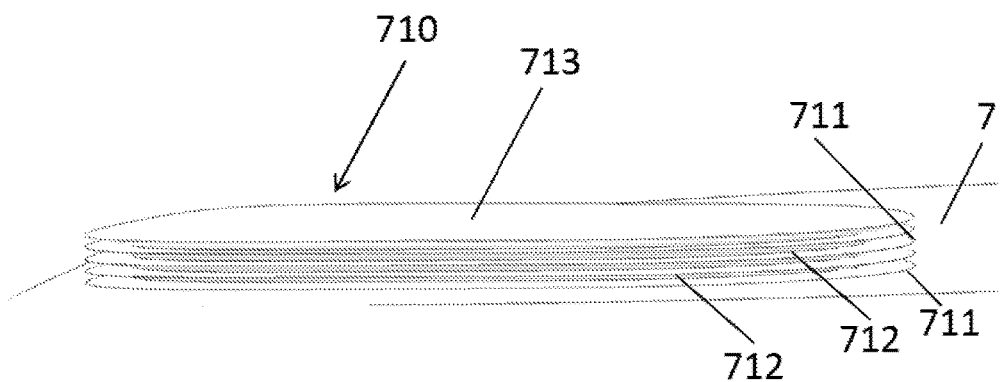
FIGS. 15a-b show one compressed and one expanded augmentation unit in the form of a chamber with a bellows-type section.
Figure 15B:
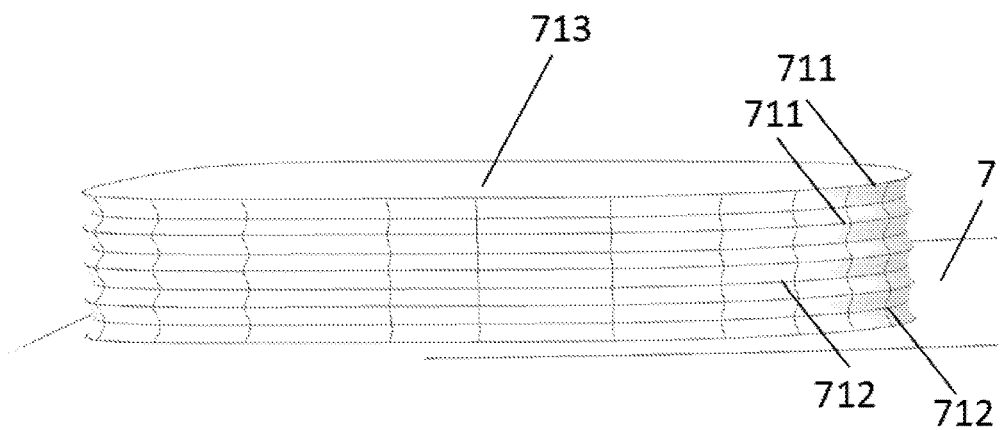

FIG. 15 shows an expandable unit (71, 72) in the form of a chamber (710). The depicted chamber is a bellows-shaped chamber (710). A bellows-shaped chamber (710) has at least one section in the form of bellows. Preferably, chamber 710 is a folding bellows consisting of one, two, three, four, five, six, seven or more folds. An outwardly bent edge (711) can be defined as a fold. An inwardly bent edge (712) can be defined as a fold. In some embodiments, the regions of the chamber wall between the folds are less stable than the folds. One, multiple or all bent edges (711, 712) can be reinforced. A reinforcement of a bent edge (711, 712) is advantageous, since the bent edge (711, 712) can be exposed to increased stress due to the expanding and relaxing of the chamber (710). A reinforcement of one or multiple bent edges (711, 712) can reduce or prevent material fatigue along the bent edge (711, 712). Reinforcement of a bent edge (711, 712) can be achieved through a greater wall thickness of the material at the bent edge (711, 712). A bent edge (711, 712) can also be reinforced through application of additional material, wherein the applied material can be the same material as the underlying material, or wherein the applied material can be a different material than the underlying material. A chamber (710) can exhibit a top side (713), a bottom side and a side surface, whereby the side surface is preferably designed in the shape of a bellows. The top (713) and/or the bottom side can be oval, circular, elliptical, or polygonal. The top side (713) can have a different shape than the bottom side.

A bellows-shaped chamber (710) can be inserted into a sheath of the type described above. The chamber (710) can be directly attached or fixed inside the sheath. The chamber (710) can be attached to structural components of the sheath, like, for example, a wire of a wire mesh, a strap of a latticework, or a structure on a sheath sleeve.

The chamber (710) can be attached to crossing points of a mesh or latticework. The sheath can be covered by a membrane, as described above. In these cases, the chamber (710) can also be attached to the membrane. The membrane can also be a bottom side of the chamber (710).

The bellows-shaped chamber (710) can also be fastened to a sleeve (7). Multiple bellows-shaped chambers (710) can be fastened to a sleeve (7). The sleeve (7) can at least partially have the shape of a heart. The sleeve (7) can have a shape similar to that of the sheath. The sleeve (7) can be inserted into the sheath. The sheath (7) can be fastened and/or fixed inside the sheath. The sleeve (7) can, in addition to one or multiple augmentation units like, for example, one or multiple bellows-shaped chambers (710), also exhibit one or multiple positioning units. The bottom side of the chamber (710) can be made of the same material as the sleeve (7). The sleeve (7) can be part of the chamber (710). The sleeve (7) can form the bottom side of the chamber. In those cases, only the lateral surfaces, which can be bellows-shaped, are applied to a sleeve (7). In addition, a top side (713) can be attached as well. The top side (713) can be a sleeve as well. Embodiments consist of two sleeves (7), whereby the sleeves (7) create the top side and the bottom side of the chambers, and lateral surfaces are formed between the sleeves. In this case, lateral surfaces can also be formed by joining, in particular by welding or gluing together of the two sleeves. The sleeves (7) can be joined together, in particular, welded or glued together, such that a chamber is formed. In some embodiments, the sleeves are connected to each other in a common edge region. In some embodiments, the chamber defines a gap of 0.1 mm to 5 mm. The line supplying the chamber can be formed similar to the chamber at least partially by joining the two sleeves (7), in particular by welding or gluing together of the two sleeves (7). Located on one of the two sleeves (7) or on both sleeves (7) can be one or multiple sensors or one or multiple electrodes.

The sleeve (7) with the expandable unit can at the upper edge and/or at the lower edge exhibit at least one pocket. The pocket can be at least partially pulled over a structural shape of a sheath. The pocket can, for example, be at least partially pulled over a loop of a wire mesh or a strap of a latticework.

The sleeve (7) with the expandable unit can contain an active agent. The sleeve (7) may, for example, contain an anti-thrombotic agent, an anti-proliferative agent, an anti-inflammatory agent, an anti-neoplastic agent, an anti-mitotic agent, an anti-microbial agent, a biofilm synthesis inhibitor, an antibiotic agent, an antibody, an anticoagulative agent, a cholesterol-lowering agent, a beta blocker, or a combination thereof. The agent is preferably provided in the form of a coating on the sleeve (7). The sleeve (7) can also be coated with extra-cellular matrix proteins, in particular, fibronectin or collagen.

FIG. 16 shows a sleeve (80) with at least one sensor (81) and/or at least one electrode (82). The 3D-shape of the sleeve (80) in FIG. 16a is comparable to the 3D-model described in FIG. 13a and shows a coordinate system as described above. The sleeve (80) can at least partially enclose a heart. The sleeve (80) can at least partially have the shape of a heart. The sleeve (80) can have a shape similar to that of the sheath. The sleeve (80) can be inserted into the sheath. The sleeve (80) can be made of a synthetic material, polymer, natural rubber, rubber, latex, silicon or polyurethane. The sleeve (80) can exhibit a thickness of 0.1 mm to 1 mm, preferably 0.2 mm to 0.5 mm. The sleeve (80) with the sensor (81) and/or the electrode (82) can be pressed against the myocardium by the sleeve with the expandable units. The sleeve (80) can be coated, in particular, with a lubricant, which reduces the friction between the myocardium and the sleeve (80) with the sensor (81) and/or the electrode (82). A coating, in particular, a coating with a lubricant can also be provided between the sleeve (80) with the sensor (81) and/or the electrode (82) and the sleeve with the expandable unit. The sensor (81) and/or the electrode (82) can be worked, molded or welded into the sleeve (80) or attached, glued onto or sewn onto the sleeve (80). The sensor (81) and/or the electrode (82) can be equipped with reinforcements configured to prevent bending during the compression of the device.

In FIG. 16a, the sleeve (80) is depicted with at least one sensor (81) and/or at least one electrode (82) as a sleeve (80) with a multiplicity of sensors (81) and electrodes (82). FIG. 16b shows a 2D-rollout of the 3D-model from FIG. 16a. The rollout depicted in FIG. 16b essentially matches the rollout of a 3D-model explained in conjunction with FIG. 13b. Unlike in FIG. 13a, the 3D-model in FIG. 16a is rotated to allow a view from above into the sleeve (80). In FIGS. 16a and 16b, eight sensors (81) or electrodes (82) are shown as examples. Other embodiments can include one, two, three, four, five, six, seven, eight, nine, ten, eleven, twelve or more sensors (81) and/or electrodes (82). The sleeve (80) with the sensor (81) or at least one electrode (82) can be a net of sensors (81) or electrodes (82). The net of sensors (81) or electrodes (82) can at least partially enclose the heart. The sensors (81) or electrodes (82) in the net of sensors (81) or electrodes (82) can be interconnected. The sleeve (80) can function as the carrier of the net of sensors (81) or electrodes (82). The net of sensors (81) or electrodes (82) can also be only partially attached to a sleeve (80). The net of sensors (81) or electrodes (82) can also be inserted without a sleeve (80) into a sheath as the one described above.

The sensor (81) or the electrode (82) can determine a physical or a chemical property of its environment. The property can be detected qualitatively or quantitatively. The sensor (81) can be an active sensor or a passive sensor. The sensor (81) can detect at least one parameter of the heart. The sensor (81) can be configured to determine the heart rate, the ventricular pressure, the systolic blood pressure, the diastolic blood pressure, pressure applied to a surface of the heart, fluid presence, acidity, electrical resistance, osmolarity, oxygen saturation or flow through a vessel. The sensor (81) can be configured to measure the pressure applied by an expandable unit onto a surface, the pH-value, the electric resistance, the osmolarity of a solution, or the flow through a vessel. The sensor can also be used as an electrode.

The electrode (82) can be configured to electrically stimulate areas of the heart and/or to measure the electrical activity at the epicardium during the excitation process. The electrode (82) can be configured to stimulate the myocardium with the use of electrical impulses. An electrical stimulation can induce a myocardium to contract. The electrode (82) can be a pacemaker electrode. The electrode (82) can be an extra-cardial stimulation electrode. With an electrode (82), the myocardium can be stimulated before, during or after a support of the pumping function of the heart by a sheath with at least one expandable unit. The expansion of an expandable unit can occur before, during or after stimulation with an electrode (82). The device for the support of the cardiac function can be operated only with at least one expandable unit or only through stimulation with at least one electrode (82). Simultaneous operation of the expandable unit and the electrode (82) can be synchronous or asynchronous. The electrode can also be used a sensor.

The sensor (81) or the electrode (82) can be fastened to the sleeve (80). The sensor (81) or the at least one electrode (82) can be glued, sewed or welded to the sleeve (80). The sensor (81) or the electrode (82) can be attached to the inside of the sleeve (80), preferably welded in. The sensor (81) or the electrode (82) can be connected via a lead (84) to a supply unit. The data detected by the sensor (81) or the electrode (82) can be transmitted connectionless via wireless technology, like bluetooth, for example.

The contacts of the electrodes or sensors or the entire sleeve can be coated with a substance, which increases or improves conductivity. A graphite coating on the contacts, for example, can increase their conductivity.

Example #1

Figure 17:
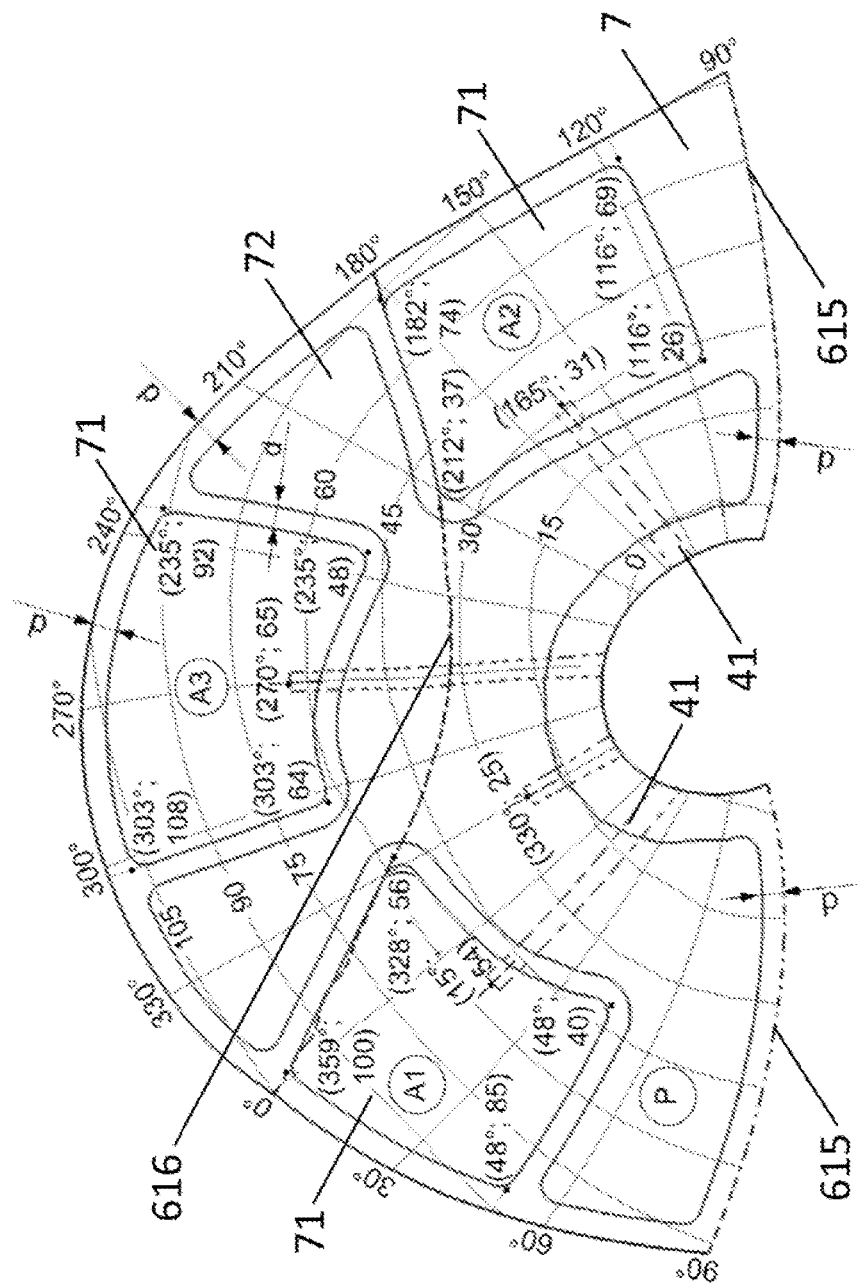
FIG. 17 shows a sample embodiment for a sleeve with augmentation and positioning units.

FIG. 17 shows an embodiment of a sleeve (7) with at least one expandable unit (71, 72). FIG. 17 depicts a 2D-rollout of a 3D-model described in conjunction with FIG. 13. The illustrated sheath includes three augmentation units (71) (A1, A2, A3) and a positioning unit (72) (P). In some embodiments, the augmentation units A1 and A2 each occupy an area of 28.6 cm$^2$ on the sleeve. The area occupied by augmentation unit A3 in this example is 34.5 cm$^2$. The positioning unit (72) (P) occupies an area 114.5 cm$^2$. Under normal conditions, the nominal expansion of the positioning unit (P) is 5 mm (e.g., the positioning unit is partially expanded and exhibits a thickness of 5 mm). The positioning unit can be a chamber, which can be filled and unfilled with a fluid. The thickness of the positioning unit can therefore be between 1 mm and 10 mm, preferably between 3 mm and 7 mm. By changing the thickness of the positioning unit (72) (P) an increase or decrease of the size of the heart can be compensated, and the correct fit of the sleeve (7) and/or the sheath essentially remains guaranteed.

In this example, the thicknesses of augmentation units A1 and A2 can be expanded by about 1.9 cm in order to build up a pressure onto a ventricle (here, the left ventricle). The effective volume expansion of the augmentation units A1 and A2 in this example is 40 ml. The effective volume expansion of the augmentation unit A3 in this example is 50 ml and leads to an effective expansion of the thickness by 1.45 cm. Every corner of an augmentation unit can be described by the coordinates of the corner points (vertices). The coordinate system has been explained in conjunction with FIG. 13.

In this example, augmentation unit A1 extends from vertex 1 ($\varphi=359°$; z=100) via vertex 2 ($\varphi=48°$; z=85) and vertex 3 ($\varphi=48°$; z=40) to vertex 4 ($\varphi=328°$; z=56), and, in the implanted state, lies flat against the left ventricle. The connection of vertex 1 to vertex 2 essentially extends parallel to the upper edge of the sleeve (7) at a distance (d) of about 5 mm. The connection of vertex 2 to vertex 3 essentially extends along the $\varphi=48°$ line. The connection of vertex 3 to vertex 4 essentially extends parallel to the upper edge of the sleeve (7) shown in the 3D-model. The connection of vertex 4 to vertex 1 essentially extends along the septal line (616). The corners of the augmentation unit A1 are rounded and describe a circular arc with a diameter of 4 mm.

In this example, augmentation unit A2 extends from vertex 1 ($\varphi=116°$; z=69) via vertex 2 ($\varphi=182°$; z=74) and vertex 3 ($\varphi=212°$; z=37) to vertex 4 ($\varphi=116°$; z=26) and, in the implanted state, lies flat against the left ventricle. The connection of vertex 1 to vertex 2 essentially extends parallel to the upper edge of the sleeve (7) at a distance (d) of about 5 mm. The connection of vertex 2 to vertex 3 essentially extends along the septal line (616). The connection of vertex 3 to vertex 4 essentially extends parallel to the upper edge of the sleeve (7) shown in the 3D-model.

The connection of vertex 4 to vertex 1 essentially extends along the $\varphi=116°$ line. The corners of the augmentation unit A2 are rounded and describe a circular arc with a diameter of 4 mm.

In this example, the augmentation unit A3 extends from vertex 1 ($\varphi=235°$; z=92) via vertex 2 ($\varphi=303°$; z=108) and vertex 3 ($\varphi=303°$; z=64) to vertex 4 ($\varphi=235°$; z=48) and, in the implanted state, lies flat against the right ventricle. The connection of vertex 1 to vertex 2 essentially extends parallel to the upper edge of the sleeve (7) at a distance (d) of about 5 mm. The connection of vertex 2 to vertex 3 essentially extends along the φ=303° line. The connection of vertex 3 to vertex 4 essentially extends parallel to the upper edge of the sleeve (7) shown in the 3D-model. The connection of vertex 4 to vertex 1 essentially extends along the φ=235° line. The corners of augmentation unit A3 are rounded and describe a circular arc with a diameter of 4 mm.

The positioning unit P in the example of FIG. 17 is designed to essentially fill the spaces between the augmentation units (71) on the sleeve (7). The positioning unit (72) can also be described as a positioning unit (72) with extensions, which fill in the areas of the sleeve (7) that are not filled by the augmentation units. In this embodiment, the positioning unit P is essentially located at a lateral distance (d) from the augmentation units (71) and the upper edge of the sleeve (7) of about 5 mm. The positioning unit (72) is also located at a distance from the cutting line (615), which can be advantageous during manufacturing. If the sleeve (7) with the expandable unit is formed in a two-dimensional state, all augmentation units (71) and positioning units (72) can be attached to the sleeve (7) before the sleeve (7) is rolled into a three-dimensional form.

In the example of FIG. 17, the lines (41) supplying the expandable units (71, 72) are hydraulic or pneumatic lines (41) extending radially from the lower edge of the sheath to the augmentation units. The line (41) for the augmentation unit A2 extends along the line φ=15° and ends at the height of z=54. The line (41) for augmentation unit A2 extends along the line φ=165° and ends at the height of z=31. The line (41) for augmentation unit A3 extends along the line φ=270° and ends at the height of z=65. The line (41) for the positioning unit P extends along the line φ=330° and ends at a height of z=25.

Example #2

Figure 18:
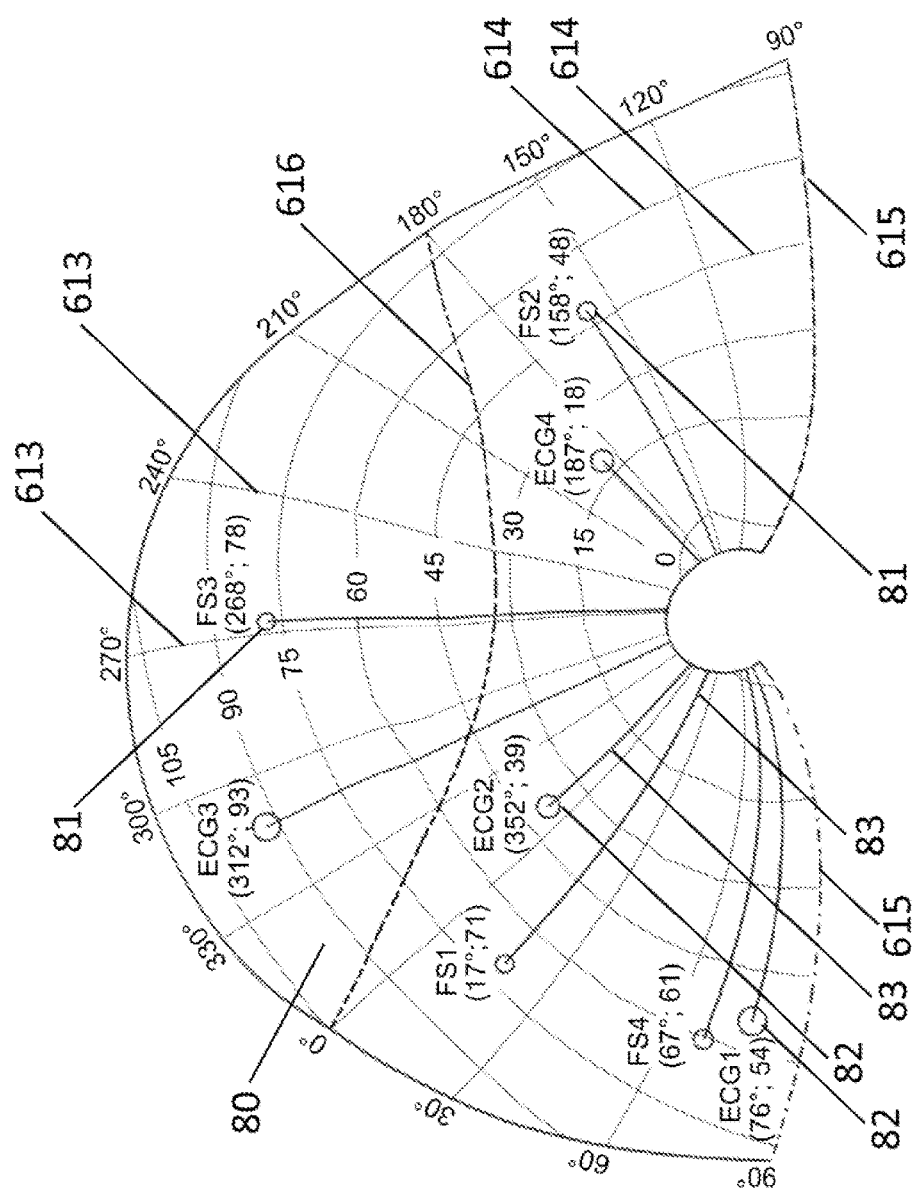
FIG. 18 shows a sample embodiment for a sleeve with sensors and electrodes.

FIG. 18 shows an embodiment for a sleeve (80) with at least one sensor (81) and/or an electrode (82). Shown in FIG. 18 is a rollout as described in conjunction with FIG. 13. The sleeve (80) of this embodiment includes eight sensors (81) or electrodes (82), whereby four of these are pressure sensors (force sensor FS1, FS2, FS3, FS4) (81), and four are electrocardiogram electrodes (e.g., ECG1, ECG2, ECG3, ECG4) (82). The sleeve (80) can be made of a synthetic material, polymer, natural rubber, rubber, latex, silicon or polyurethane. The sleeve (80) can have a thickness of 0.1 to 1 mm, preferably 0.2 mm to 0.5 mm. The four pressure sensors (81) can be integrated into the sleeve (80), for example, molded or welded to the inside surface of the sheath. The pressure sensors (81) can be equipped with reinforcements, which can prevent bending during the compression of the device. The ECG electrodes (82) can be attached at the side of sleeve (80) facing the heart. In the embodiment in FIG. 18, a system of coordinates is depicted as described in conjunction with FIG. 13. Using the coordinate system, the positions of the sensors (81) and electrodes (82) can be determined as follows: pressure sensor FS1 is located at coordinate (φ=17°; z=71), pressure sensor FS2 is located at coordinate (φ=158°; z=48), pressure sensor FS3 is located at coordinate (φ=268°; z=78), pressure sensor FS4 is located at coordinate (φ=67°; z=61). ECG electrode ECG1 is located at coordinate (φ=76°; z=54), ECG electrode ECG2 is located at coordinate (φ=352°; z=39), ECG electrode ECG3 is located at coordinate (φ=312°; z=93) and ECG electrode ECG4 is located at coordinate (φ=187°; z=18). For smaller or larger hearts, the angular coordinates for the sensors (81) and/or electrodes (82) essentially remain the same; while the z-value is scaled by a factor. For example, for smaller hearts, the scaling factor can be between 0.85 and 0.95, and for larger hearts, the scaling factor can be between 1.05 and 1.15.

What is claimed is:

1. A heart support system comprising:
   a heart-shaped cup comprising
      a self-expanding sheath sized to fit about at least a portion of a heart in a living body, the self-expanding sheath having an internal contour that corresponds to an outer contour of the heart,
      a plurality of expandable chambers each disposed at least in part on the self-expanding sheath so as to apply pressure against the heart when expanded, and
      at least one sensor to be held in contact with a surface of the heart;
   a conduit comprising
      at least one pressurized fluid line for communicating pressurized fluid to the plurality of expandable chambers, and
      at least one electrical connection port for communicating signals from the at least one sensor;
   a supply unit comprising
      a fluid reservoir for delivering the pressurized fluid to the plurality of expandable chambers,
      processing circuitry for receiving signals from the at least one sensor, and
      a supply unit connector for connecting the conduit to the supply unit;
   wherein the conduit fluidically and electrically connects the heart-shaped cup to the supply unit such that all inputs and outputs to the heart-shaped cup are communicated via the conduit; and
   wherein, in an expanded state, the heart-shaped cup has an internal contour that corresponds to an outer contour of the living heart such that a gap between the outer contour and the internal contour is at all points less than 8 mm.

2. The heart support system of claim 1, wherein:
   the conduit comprises
      a first section spanning from the heart-shaped cup to a first connector, and
      a second section spanning from a second connector to the supply unit; and
   the heart support system further comprises a securing mechanism for securing connection of the first connector to the second connector.

3. The heart support system of claim 2, wherein:
   one of the first connector and the second connector comprises at least one guide peg; and
   the other of the first connector and the second connector comprises at least one guide slot, wherein
      the at least one guide slot is configured to slideably mate with the at least one guide peg when the first connector is connected to the second connector.

4. The heart support system of claim 1, wherein the conduit comprises a flexible cable.

5. The heart support system of claim 4, wherein the cable is coated with a cable coating.

6. The heart support system of claim 5, wherein the cable coating comprises a coating material selected from the group consisting of polyurethane, silicon, polytetrafluoroethylene, polyethylene, polypropylene, polyethylene terephthalate, polycarbonate, and polyamide.

7. The heart support system of claim 4, wherein the cable is reinforced with a fabric.

8. The heart support system of claim 1, wherein the supply unit is disposed at least partially within the living body.

9. The heart support system of claim 1, wherein the conduit comprises multiple pneumatic connection ports each in hydraulic communication with a different expandable chamber of the plurality of expandable chambers.

10. The heart support system of claim 1, wherein the supply unit further comprises an electrical line in electrical communication with the at least one sensor through the at least one electrical connection port.

11. The heart support system of claim 10, wherein each electrical connection port comprises a sealing surface.

12. The heart support system of claim 1, wherein the at least one pneumatic connection port and the at least one electrical connection port each include a seal.

13. The heart support system of claim 1, wherein the self-expanding sheath is sized with a scaling factor relative to a 3D-image of the surface of the heart.

14. A method of supporting a heart, the method comprising:
  inserting a heart constraint into a living body, the heart constraint comprising a self-expanding sheath,
    a plurality of expandable chambers each disposed at least in part on the self-expanding sheath,
    at least one sensor, and
    a conduit comprising
      at least one pressurized fluid line for communicating pressurized fluid to the plurality of expandable chambers, and
      at least one electrical lead for communicating signals from the at least one sensor;
  positioning the heart constraint about at least a portion of a heart within the body, with the at least one sensor disposed against the heart;
  connecting a terminal connector of the conduit to a single connector of a housing, the housing comprising
    a pressurized fluid source for delivering the pressurized fluid to the plurality of expandable chambers through the single connector, and
    a microprocessor for receiving signals from the at least one sensor through the single connector; and
  expanding the plurality of expandable chambers to apply pressure to the heart, by causing pressurized fluid to flow from the pressurized fluid source through the single connector and through the conduit into the plurality of expandable chambers, such that the at least one sensor is held in contact with the heart;
    wherein the self-expanding sheath has an internal contour that corresponds to an outer contour of the heart such that a spacing between the outer contour and the inner contour is substantially constant and wherein the heart constraint is held in place surrounding the heart absent an adhesive.

15. The method of claim 14, further comprising implanting the housing within the living body.

16. The method of claim 14, wherein:
  the plurality of expandable chambers comprise two or more separately expandable chambers; and
  connecting the conduit to the single connector comprises connecting the pressurized fluid source to multiple pneumatic connection ports of the single connector, wherein
    each pneumatic connection port is in hydraulic communication with a different expandable chamber of the plurality of expandable chambers.

17. The method of claim 14, further comprising:
  connecting a first section of the conduit spanning from the heart constraint to a first connector to a second section of the conduit spanning from a second connector to the housing.

18. The method of claim 17, wherein:
  a first pneumatic connection port of the first connector connects with a second pneumatic connection port of the second connector, wherein
    the first pneumatic connection port is in hydraulic communication with the pressurized fluid source through a pneumatic supply line, and
    the second pneumatic connection port is in hydraulic communication with a first expandable chamber of the plurality of expandable chambers.

19. The method of claim 18, wherein inserting the heart constraint comprises:
  inserting a catheter into the body and into a pericardium, a lumen of the catheter encasing the self-expanding sheath in a non-expanded state; and
  inserting the self-expanding sheath into the body and into the pericardium via the catheter;
  wherein, upon inserting, the self-expanding sheath automatically transforms from the non-expanded state to the expanded state.

20. The method of claim 17, wherein:
  a first electrical connection port of the first connector connects with a second electrical connection port of the second connector, wherein
    the first electrical connection port is in electrical communication with the microprocessor, and
    the second electrical connection port is directly connected to the at least one sensor via a lead.

21. The method of claim 14, further comprising:
  receiving a virtual or real image of the heart;
  forming the self-expanding sheath based on a shape of the heart image;
  wherein the self-expanding sheath is configured to expand into a shape similar to the shape of the heart image.

* * * * *